(12) United States Patent
Mathews

(10) Patent No.: US 11,350,956 B2
(45) Date of Patent: Jun. 7, 2022

(54) SNARE DEVICE WITH ANTI-SKEWING

(71) Applicant: Carnelian Medical LLC, Walpole, MA (US)

(72) Inventor: Eric D. Mathews, Walpole, MA (US)

(73) Assignee: CARNELIAN MEDICAL LLC, Walpole, MA (US)

( * ) Notice: Subject to any disclaimer, the term of this patent is extended or adjusted under 35 U.S.C. 154(b) by 504 days.

(21) Appl. No.: 16/528,814

(22) Filed: Aug. 1, 2019

(65) Prior Publication Data

US 2021/0030431 A1 Feb. 4, 2021

(51) Int. Cl.
*A61B 17/221* (2006.01)
*A61B 17/00* (2006.01)

(52) U.S. Cl.
CPC .. *A61B 17/221* (2013.01); *A61B 2017/00398* (2013.01); *A61B 2017/00862* (2013.01); *A61B 2017/00867* (2013.01); *A61B 2017/2212* (2013.01)

(58) Field of Classification Search
CPC .............. A61B 17/124; A61B 17/1245; A61B 17/12154; A61B 2017/22031; A61B 2017/22034; A61B 2017/22035; A61B 2017/2212; A61B 2017/2215; A61B 2017/2217; A61M 2025/09058; A61M 2025/09083; A61M 2025/09191
See application file for complete search history.

(56) References Cited

U.S. PATENT DOCUMENTS

| 5,551,443 | A | 9/1996 | Sepetka et al. |
|---|---|---|---|
| 6,074,378 | A | 6/2000 | Mouri et al. |
| 6,391,018 | B1 | 5/2002 | Tanaka et al. |
| 6,500,185 | B1 | 12/2002 | Mathews et al. |
| 6,620,172 | B1 | 9/2003 | Dretler et al. |
| 6,652,536 | B2 | 11/2003 | Mathews et al. |
| 7,058,456 | B2 | 6/2006 | Pierce |
| 2002/0161397 | A1* | 10/2002 | Mathews .............. A61B 17/221 606/200 |
| 2004/0225269 | A1* | 11/2004 | Zhao ........................ B29B 9/12 264/479 |

(Continued)

OTHER PUBLICATIONS

International Search Report in PCT Application No. PCT/US2020/044469 dated Oct. 15, 2020.

(Continued)

*Primary Examiner* — Martin T Ton
(74) *Attorney, Agent, or Firm* — Kriegsman & Kriegsman

(57) ABSTRACT

Snare device with anti-skewing. In one embodiment, the snare device includes a core-wire. The core-wire is made of a superelastic material and includes a proximal portion of greater cross-sectional area and a distal portion of lesser cross-sectional area. The distal portion includes a looped shape in a relaxed state. A flexible coil is mounted around the core-wire and is straight in a compressed state. The distal ends of the core-wire and the coil are coupled together. The proximal end of the core-wire is coupled to a handle of an actuator, and the proximal end of the coil is coupled to a slide of an actuator, the slide being slidably mounted on the handle. The tensile strength of the coil multiplied by the cross-sectional area of the coil is greater than the upper plateau stress of the core-wire distal portion multiplied by the cross-sectional area of the core-wire distal portion.

17 Claims, 13 Drawing Sheets

(56) References Cited

U.S. PATENT DOCUMENTS

| | | | |
|---|---|---|---|
| 2006/0200171 A1* | 9/2006 | Teague | A61B 17/221 606/127 |
| 2006/0229638 A1 | 10/2006 | Abrams et al. | |
| 2008/0275464 A1* | 11/2008 | Abrams | A61B 17/221 606/113 |
| 2009/0209987 A1 | 8/2009 | Mathews et al. | |
| 2013/0190772 A1* | 7/2013 | Doerr | A61B 17/864 606/104 |
| 2015/0290432 A1 | 10/2015 | Mathews et al. | |

OTHER PUBLICATIONS

Written Opinion in PCT Application No. PCT/US2020/044469 dated Oct. 15, 2020.

* cited by examiner

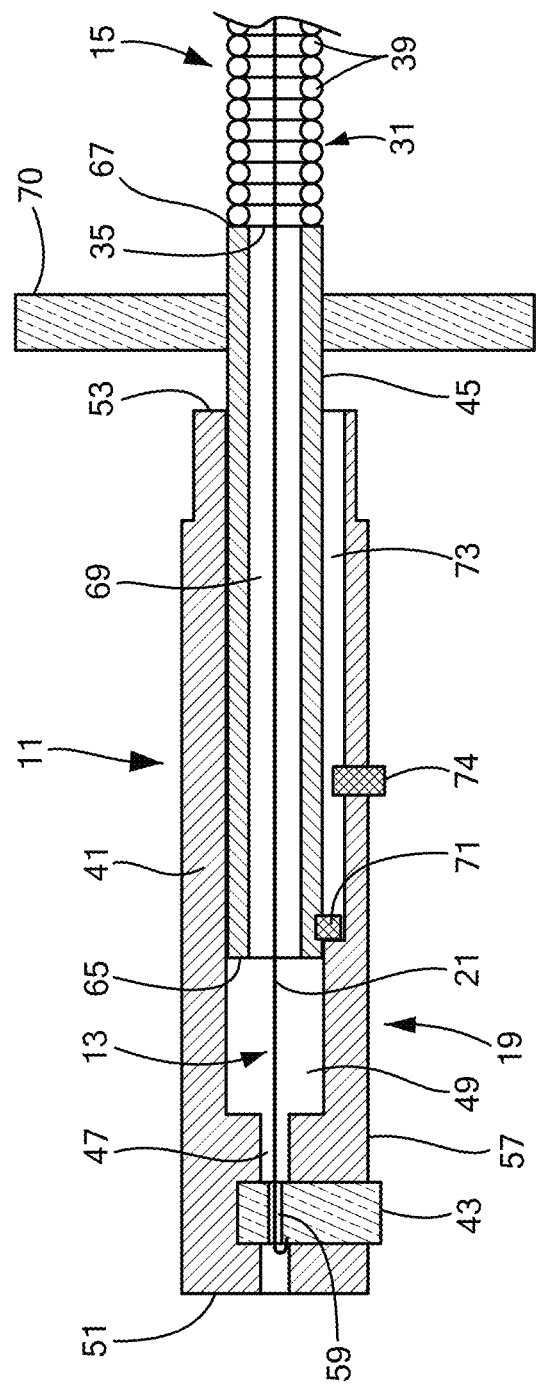
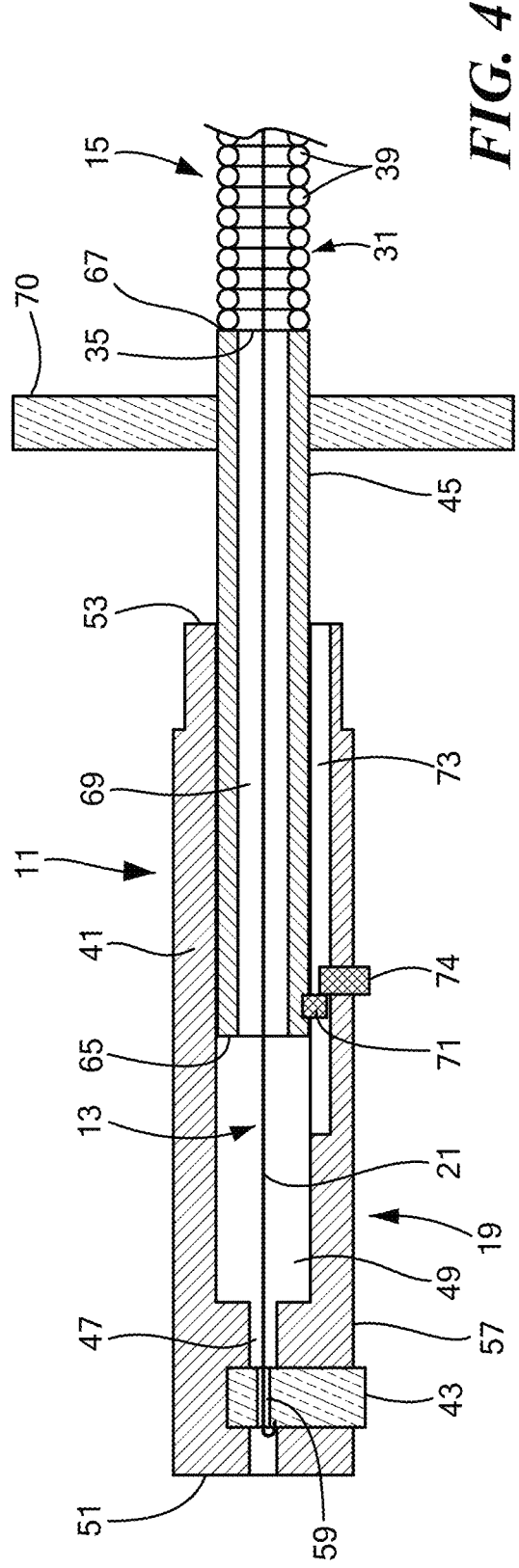
FIG. 3
FIG. 4

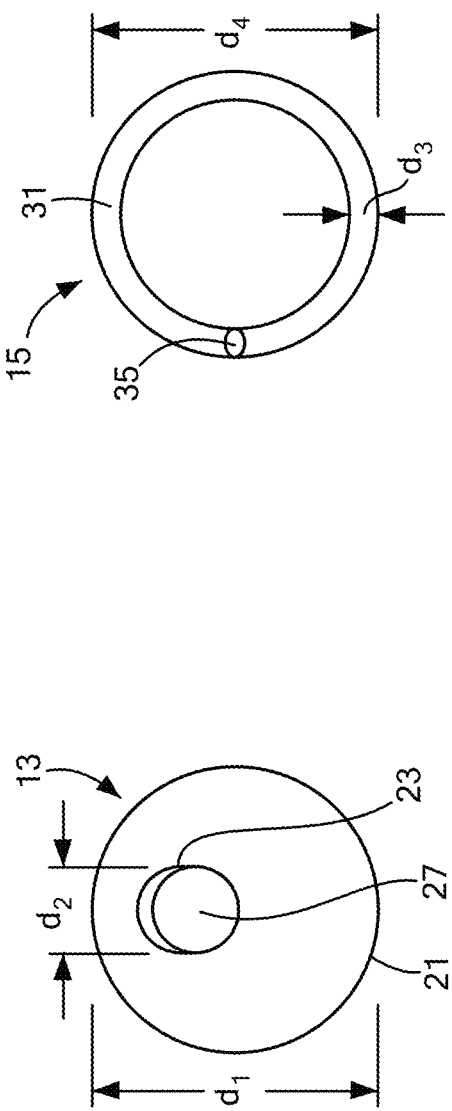
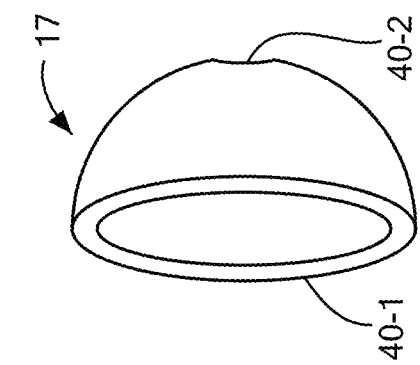
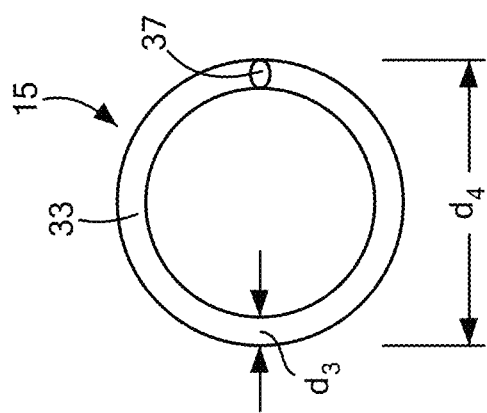

SNARE DEVICE WITH ANTI-SKEWING

BACKGROUND OF THE INVENTION

The present invention relates generally to snare devices and relates more particularly to a novel snare device.

There are many situations in which it may be desirable to capture or to retrieve an object from a confined space. For example, in the field of medicine, it may be desirable, in some instances, to capture and to remove a blood clot from a blood vessel. To this end, a number of snare devices have been devised.

One example of a snare device is disclosed in U.S. Pat. No. 6,500,185 B1, inventors Mathews et al., which issued Dec. 31, 2002, and which is incorporated herein by reference. According to U.S. Pat. No. 6,500,185 B1 (hereinafter "the '185 patent"), the snare device has a longitudinally extending support that defines an axis. The support has a flexible distal section and a rigid proximal section. The flexible distal section, which is in the form of a coiled wire, has a compressed state, in which it defines a first path relative to the axis. A core-wire extending along the axis has a relaxed state in which it defines a second path relative to the axis. An anchor disposed on the flexible distal section and attached to the core-wire causes the flexible distal section to follow the same path. An actuator engaged to a proximal end of the core-wire enables a surgeon to selectively apply a tensile force thereto. This tensile force causes the core-wire and the flexible distal section to transition together between the first path and the second path.

According to the '185 patent, a suitable outer overall diameter for the support of the snare device is approximately 0.014 inch, which renders the device suitable for general intravascular use. In addition, according to the '185 patent, a suitable material for forming the coiled wire support is a platinum alloy, which is radiopaque, thereby enabling a surgeon to track the position of the snare device within a body.

Another example of a snare device is disclosed in U.S. Patent Application Publication No. US 2006/0229638 A1, inventors Abrams et al., which was published Oct. 12, 2006, and which is incorporated herein by reference. According to U.S. Patent Application Publication No. US 2006/0229638 A1 (hereinafter "the '638 publication"), device and methods for removing a foreign object from a body lumen are disclosed. A retrieval device in accordance with an exemplary embodiment includes an elongated member including a flexible collector element and a core-wire that can be engaged by a physician to actuate the collector element between a first position and a second position with the body. The collector element may comprise a coiled section including a coiled flat ribbon of rectangular cross-section adapted to assume a substantially straight shape in the first position and an expanded shape forming one or more helically oriented loops in the second position. According to the '638 publication, stainless steel is a suitable material for the elongated member including the collector element.

One problem that has been noted with snare devices of the types discussed in the '185 patent and in the '638 publication is a phenomenon sometimes referred to as "skewing." More specifically, where the flexible distal section of the support is in the form of a coiled wire, as the coiled wire transitions from the first path to the second path, some of the turns of the coiled wire may be subjected to inwardly-directed radial forces. If these forces are sufficiently great, they can cause one or more of the turns to be radially displaced inwardly or "skewed" relative to their neighboring turns. Such skewing is undesirable for at least a couple of reasons. For one thing, a skewed turn of the coiled wire may come into contact with the core-wire in such a way as to inhibit the ability of the core-wire to transition properly from its first path to its second path. In addition, a skewed turn of the coiled wire may result in permanent misalignment of the turns of the coiled wire, thereby impairing the ability of the coiled wire to transition properly between the first and second paths.

In U.S. Pat. No. 6,652,536 B2, inventors Mathews et al., which issued Nov. 25, 2003, and which is incorporated herein by reference, some different approaches to the above-described problem of skewing in a snare device are disclosed. According to U.S. Pat. No. 6,652,536 B2 (hereinafter "the '536 patent"), one approach is to dimension the diameter of the lumen of the coiled wire small enough relative to the outer diameter of the core-wire so as to prevent one or more turns of the coiled wire from migrating radially inwardly to an extent that skewing may occur. At the same time, the diameter of the lumen of the coiled wire is dimensioned to be large enough relative to the outer diameter of the core-wire to keep the coiled wire and the core-wire from binding with each other as the snare device is in use.

Another approach that is disclosed in the '536 patent is to position a spacer coil around the core-wire, the spacer coil being made of, or having a portion made of, a radiopaque material, such as platinum. The spacer coil can either be in contact with the core-wire or be separated therefrom by a clearance that is small enough to prevent turns of the spacer coil from, themselves, becoming radially displaced relative to the core-wire. The spacing between the coiled wire and the spacer coil is selected to be small enough to prevent a turn of the coiled wire from becoming radially displaced to an extent sufficient to allow adjacent turns of the coiled wire to come into contact with one another, thereby causing the intervening turn to be permanently skewed out of alignment. However, the spacing between the spacer coil and the coiled wire is also selected to be large enough so that the spacer coil and the coiled wire do not bind with each other as the device is in use.

Although the approaches disclosed in the '536 patent may ameliorate the problem of skewing to a certain extent, the present inventor also believes that these approaches may be impractical in certain cases. For example, the use of a spacer coil increases the distal stiffness of the device, particularly when compressed/tensioned, thereby making the device more difficult to deliver through a tortuous lumen to an obstruction that requires snaring. Additionally, the increased friction between the spacer coil and the support coil inhibits the device from transitioning from its straight configuration to its relaxed coiled configuration. Moreover, the use of a spacer coil increases the manufacturing cost and complexity of the device and also introduces some potential problems, such as the skewing of the spacer coil, itself. Therefore, the present inventor believes that there is a need for an alternative approach to minimizing the occurrence and effects of skewing.

Other documents of interest may include the following, all of which are incorporated herein by reference: U.S. Pat. No. 7,058,456 B2, inventor Pierce, which issued Jun. 6, 2006; U.S. Pat. No. 6,620,172 B 1, inventors Dretler et al., which issued Sep. 16, 2003; and U.S. Patent Application Publication No. US 2009/0209987 A1, inventors Mathews et al., which was published Aug. 20, 2009.

SUMMARY OF THE INVENTION

It is an object of the present invention to provide a novel snare device or similar instrument.

According to one aspect of the invention, there is provided an instrument, such as snare device, the instrument comprising: (a) a longitudinally extending support defining an axis, the support having an uncompressed state of comparatively greater length and a compressed state of comparatively lesser length, the support comprising a flexible distal section, the flexible distal section comprising a coiled filament of round cross-sectional shape and defining a first path relative to the axis when in the compressed state, the flexible distal section having a tensile strength, a filamentary cross-sectional area, and a break load, wherein the break load of the flexible distal section is equal to the tensile strength of the flexible distal section multiplied by the filamentary cross-sectional area of the flexible distal section; (b) a core-wire extending along the axis and anchored to the flexible distal section of the support, the core-wire having a relaxed state of comparatively lesser length and a tensioned state of comparatively greater length, the core-wire comprising a proximal portion and a distal portion, the distal portion of the core-wire defining a second path relative to the axis when in the relaxed state, wherein the second path differs from the first path and includes a looped shape, wherein the distal portion of the core-wire has a filamentary diameter and a filamentary cross-sectional area, wherein the distal portion of the core-wire also has an upper plateau stress in response to a tensile force applied thereto, wherein a plateau force of the distal portion of the core-wire is equal to the upper plateau stress multiplied by the filamentary cross-sectional area of the distal portion of the core-wire, wherein the distal portion of the core-wire has a length, and wherein the filamentary diameter of the distal portion of the core-wire is substantially uniform over the length of the distal portion of the core-wire in the relaxed state; and (c) an actuator secured to a proximal end of the core-wire and to a proximal end of the support to selectively apply both a tensile force to the core-wire and a compressive force to the support, the tensile force causing the core-wire to transition from its relaxed state to its tensioned state, the compressive force causing the support to transition from its uncompressed state to its compressed state; (d) wherein the break load of the flexible distal section of the support is greater than the plateau force of the distal portion of the core-wire.

In a more detailed feature of the invention, the support may terminate distally at a distal end, the core-wire may terminate distally at a distal end, and the distal end of the core-wire may be anchored to the distal end of the support.

In a more detailed feature of the invention, the support may terminate distally at a distal end, the core-wire may terminate distally at a distal end, and the distal end of the core-wire may be anchored to the support at a distance proximal to the distal end of the support.

In a more detailed feature of the invention, the looped shape may be generally circular. In a more detailed feature of the invention, the looped shape may comprise a conical helix.

In a more detailed feature of the invention, the looped shape may comprise a cylindrical helix.

In a more detailed feature of the invention, the looped shape may comprise a proximal cylindrical helix and a distal conical helix.

In a more detailed feature of the invention, the proximal portion of the core-wire may have a first strain in response to a tensile force, the distal portion of the core-wire may have a second strain in response to the tensile force, and the first strain may be less than the second strain.

In a more detailed feature of the invention, the core-wire may comprise a superelastic material, the first strain may be in an initial elastic region, and the second strain may be in a superelastic region.

In a more detailed feature of the invention, the core-wire may be a one-piece structure comprising a nickel-titanium alloy, the proximal portion of the core-wire may have a filamentary diameter of comparative greater dimension, and the distal portion of the core-wire may have a filamentary diameter of comparatively lesser dimension.

In a more detailed feature of the invention, at least a portion of the core-wire may be coated with a lubricious coating.

In a more detailed feature of the invention, the first path may be a straight line.

In a more detailed feature of the invention, the support may further comprise a proximal portion, and the proximal portion of the support and the distal portion of the support may form a one-piece structure.

In a more detailed feature of the invention, the support may further comprise a sleeve, and the sleeve may be disposed around at least one of the proximal portion of the support and the distal portion of the support.

In a more detailed feature of the invention, the actuator may comprise a handle and a slide, the slide may be slidably mounted on the handle to be selectively moved proximally and distally, the proximal end of the core-wire may be coupled to the handle, and the proximal end of the support may be coupled to the slide.

In a more detailed feature of the invention, the actuator may further comprise an anchor, the proximal end of the core-wire may be secured to the anchor, and the anchor may be rotatably mounted on the handle, whereby tension applied to the core-wire may be adjusted by rotating the anchor.

In a more detailed feature of the invention, the instrument may further comprise a spacer coil mounted around the distal portion of the core-wire and interior relative to the support.

For purposes of the present specification and claims, various relational terms like "top," "bottom," "proximal," "distal," "upper," "lower," "front," and "rear" may be used to describe the present invention when said invention is positioned in or viewed from a given orientation. It is to be understood that, by altering the orientation of the invention, certain relational terms may need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. These drawings are not necessarily drawn to scale, and certain components may have undersized and/or oversized dimensions for purposes of explication. In the drawings wherein like reference numerals represent like parts:

FIG. 3 is an enlarged fragmentary section view of a proximal portion of the snare device of FIG. 1, the snare device being shown in its coiled state;

FIG. 4 is an enlarged fragmentary section view of a proximal portion of the snare device of FIG. 1, the snare device being shown in its straightened state;

FIG. 8 is a distal end view of the core-wire shown in FIG. 6, the inner-core wire being shown in its straightened state;

FIG. 9 is a proximal end view of the support shown in FIG. 6, the support being shown in its compressed state;

FIG. 10 is a distal end view of the support shown in FIG. 6, the support being shown in its compressed state;

FIG. 11 is an enlarged perspective view of the end cap shown in FIG. 1;

DETAILED DESCRIPTION OF THE INVENTION

Figure 1:
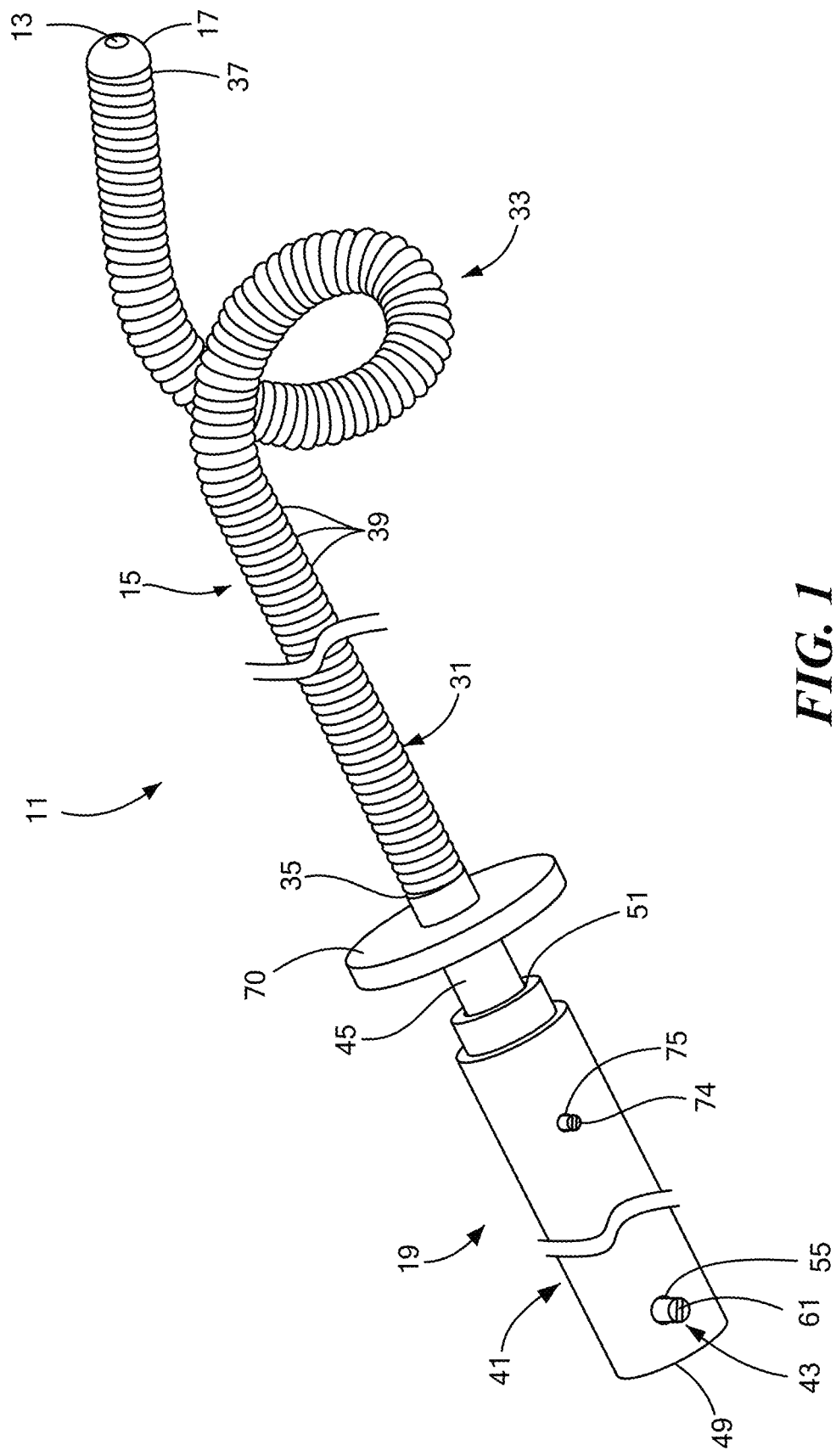
FIG. 1 is a fragmentary perspective view of a first embodiment of a snare device constructed according to the teachings of the present invention, the snare device being shown in its coiled state.
Figure 2:
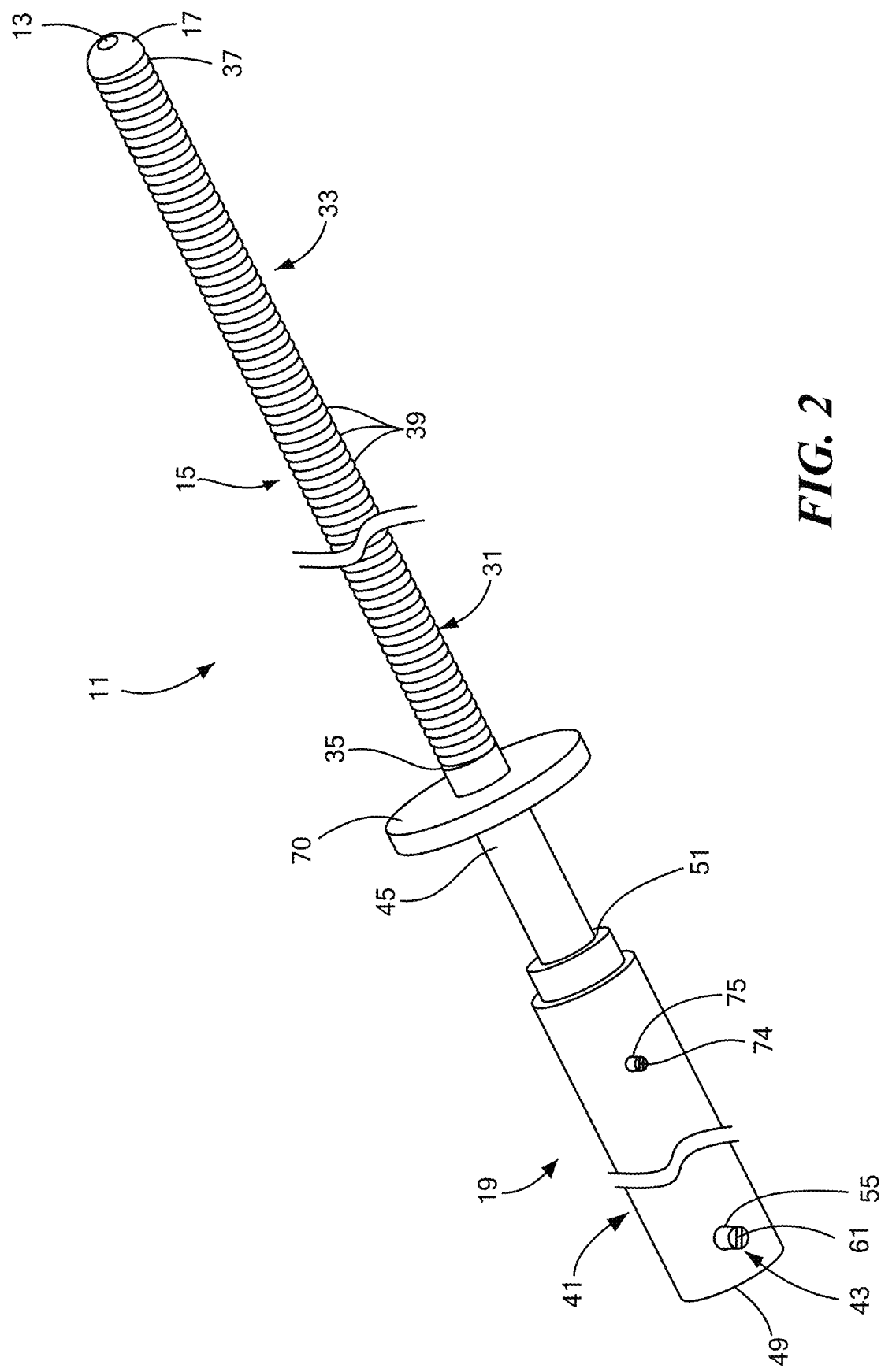
FIG. 2 is a fragmentary perspective view of the snare device of FIG. 1, the snare device being shown in its straightened state.

NITINOL™ nickel-titanium alloy is often used in medical devices in its superelastic state, where the austenite finish temperature ($A_f$) is less than room or body temperature. When a tensile force is applied to a NITINOL™ wire, the material may be elongated as much as 8% and then return to nearly its original length. In fact, when the tensile force applied causes the wire to reach its loading plateau (~2% elongation), there is a small amount of hysteresis that is experienced in the wire when the force is released. In order to incur no hysteresis in the wire length, the tensile force must be somewhat less than the amount required to reach the loading plateau. When a wire is processed so that one segment is smaller in diameter than another segment, both states (i.e., hysteresis and no hysteresis) may be achieved when applying a certain tensile force.

Additionally, superelastic NITINOL™ may be shaped using heat to form complex geometries. In this application, the distal section of a NITINOL™ wire may be shaped into forms that are advantageous for medical procedures. Such shapes may include a cylindrical helix, a conical helix, and other rounded shapes that have smooth transitions. Sharp bends in the shape are generally not conducive to the embodiments described herein.

Superelastic NITINOL™ is often used to access locations within the human body. When a NITINOL™ core-wire is placed within a coil and attached at a distal location, it is possible to apply a tensile force to the core-wire while also applying a compressive force to the coil. In this application, the NITINOL™ core-wire may have a distal section and a proximal section, where the distal section may be made smaller than the proximal section. The distal section may also be set into a complex shape as described above, and the distal section of the coil may follow the complex shape, thereby resulting in gap spacing between the coils. An actuator may be positioned proximally, attaching to both the core-wire and the coil in order to apply a tensile force to the core-wire and a compressive force to the coil.

When the actuator applies tensile and compressive forces to the core-wire and the coil, respectively, the core-wire may begin to translate within the coil, the distal coil gaps may begin to close, and the distal complex shape may move from complex to straight as the coils may become stacked in their fully compressed state. The distal core-wire may be constrained within the compressed coil and may be mostly, though not completely, straight. The applied force may tension the distal, smaller core-wire portion onto its loading plateau while the proximal portion may be tensioned an amount that does not reach its loading plateau but may remain fully elastic with no hysteresis.

While actuated, if the distal portion experiences an external force that impacts the compressed coil, the coil may translate radially or become skewed. When this occurs, individual turns of the coil may become positioned inside and outside the original outer diameter and may grab onto the core-wire. The device then may become stuck and not translatable. The present inventor has discovered that, if the break load, relating to the ultimate tensile strength of the coil, exceeds the tensile force required for the distal core-wire to reach the loading plateau, skews will not occur or will occur with a dramatically reduced frequency. In the devices of the present invention, the coil may be selected so that its break load is greater than the distal core-wire loading plateau force. This provides sufficient headroom in the event that the complex shape of the core-wire requires a tensile force exceeding the loading plateau to be applied (where the elongation is between 6-8%).

Because of these force requirements and limitations, the actuator may then be tuned to apply only the tensile/compression forces that are required to compress the coil which straightens the device. If the actuator applied a force greater than required for straightness, there would be a risk of unwanted core-wire hysteresis and coil skewing that prevents the usefulness of the device.

Thus, the present invention is directed at addressing the problem of skewing that commonly occurs in snare devices of the type described above, as well as in similar instruments. As noted above, when such devices transition from a coiled state to a straightened state, if the support comprises a coil and if the coil is subjected to inwardly-directed radial forces of sufficient magnitude, one or more of the turns of the coil may become radially displaced inwardly or "skewed" relative to their neighboring turns. Such skewing of the coil is undesirable as it may cause the coil wire to bind with the core-wire, thereby impairing the ability of the core-wire to transition properly from its coiled state to its straightened state. In addition, such skewing of the coil wire may result in permanent misalignment of the turns of the coil, thereby impairing the ability of the coil to transition properly between its coiled state and its straightened state.

As noted above and as will be discussed further below, according to the present invention, it has been found that, unexpectedly, the aforementioned problem of skewing may be ameliorated when the distal portions of the coil and the core-wire (i.e., the respective portions of the coil and the core-wire that transition between coiled and straightened states) are selected such that the following relationship exists therebetween:

Break Load$_{(distal portion\ of\ coil)}$>Plateau Force$_{(distal\ portion\ of\ core\text{-}wire)}$ wherein the break load of the distal portion of the coil is equal to the tensile strength of the distal portion of the coil multiplied by the filamentary cross-sectional area of the distal portion of the coil, wherein the distal portion of the core-wire has a filamentary cross-sectional area and also has an upper plateau stress in response to a tensile force applied thereto, and wherein the plateau force of the distal portion of the core-wire is equal to the upper plateau stress multiplied by the filamentary cross-sectional area of the distal portion of the core-wire.

Referring now to FIGS. 1 through 6, there are shown various views of a first embodiment of a snare device, the snare device being constructed according to the teachings of the present invention and being represented generally by reference numeral 11. Details of snare device 11 that are discussed elsewhere in this application or that are not critical to an understanding of the invention may be omitted from one or more of FIGS. 1 through 6 and/or from the accompanying description herein or may be shown in one or more of FIGS. 1 through 6 and/or described herein in a simplified manner.

Snare device 11 may comprise a core-wire 13, a support 15, an end cap 17, and an actuator 19.

Figure 7:
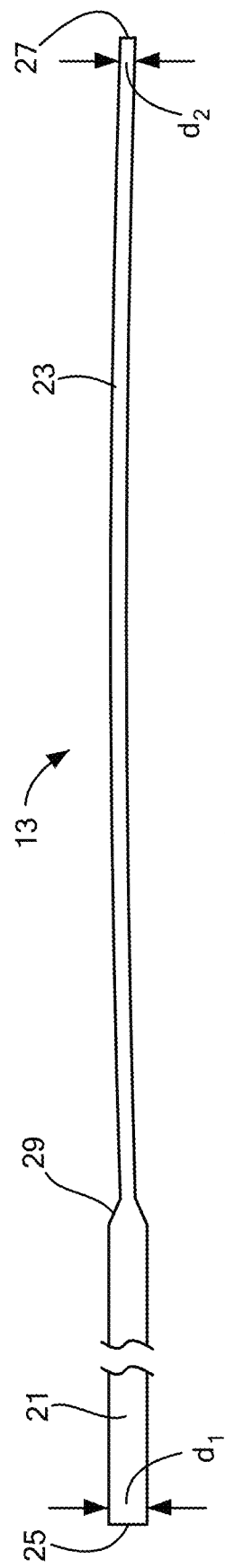
FIG. 7 is a fragmentary side view of the core-wire shown in FIG. 6, the inner-core wire being shown in its straightened state.

Core-wire 13, which is also shown separately in FIGS. 7 and 8, may be an elongated, flexible, inhomogeneous filamentary structure that is capable of transitioning from a relaxed state to a tensioned state when subjected to a threshold tensile or pulling force. In the present embodiment, core-wire 13 may comprise a proximal portion 21 and a distal portion 23. Proximal portion 21 may terminate proximally at a proximal end 25 of core-wire 13, and distal portion 23 may terminate distally at a distal end 27 of core-wire 13. Proximal portion 21 and distal portion 23 may be contiguous with one another or may be interconnected by a short intermediate portion 29. In the present embodiment, proximal portion 21 may be characterized by having a first strain in response to a given tensile force (which first strain may be uniform along the entire length of proximal portion 21), and distal portion 23 may be characterized by having a second strain in response to the same tensile force (which second strain may be uniform along the entire length of distal portion 23), wherein the first strain of proximal portion 21 is less than the second strain of distal portion 23. As a result of the disparity in the first strain and the second strain, when core-wire 13 is subjected to a tensioning force, distal portion 23 tends to stretch more than does proximal portion 21. In the present embodiment, the first strain of proximal portion 21 may be in the initial elastic region (i.e., completely reversible length, no permanent elongation) whereas the second strain of distal portion 23 may be in the superelastic region (i.e., some permanent elongation).

Proximal portion 21 of core-wire 13 may have a relaxed state in which it is substantially straight in overall shape, and distal portion 23 of core-wire 13 may have a relaxed state in which it includes a looped or coiled shape. In the present embodiment, the looped or coiled shape of distal portion 23, in the relaxed state, may be a generally circular shape. In other embodiments, which are discussed further below, the looped or coiled shape of distal portion 23 may comprise a conical helix, a cylindrical helix, other rounded shapes, or combinations thereof. When core-wire 13 is pulled to its tensioned state, distal portion 23 may lengthen, and its looped or coiled shape may substantially straighten. (To the extent that proximal portion 21 may also lengthen, such lengthening may be minor or negligible as compared to that experienced by distal portion 23.)

In the present embodiment, core-wire 13 may be a unitary or one-piece structure made of a super-elastic and shaped-memory material. Such a material has the property that, when deformed and heated past a critical temperature, it "remembers" its deformed state. When cooled and subjected to further deformation, such a material springs back to this remembered shape. A suitable super-elastic material from which core-wire 13 may be manufactured is a nickel-titanium alloy commonly sold under the trade name NITINOL™. In the case of the aforementioned nickel-titanium alloy, the critical temperature is in the neighborhood of 700-1020 degrees Fahrenheit.

Where, as described above, core-wire 13 is a unitary structure made of a super-elastic, memory-shaped material, the difference in yield forces between proximal portion 21 and distal portion 23 may be achieved by providing proximal portion 21 with a first filamentary cross-sectional diameter $d_1$, which may be substantially uniform along the entire length of proximal portion 21, and by providing distal portion 23 with a second filamentary cross-sectional diameter $d_2$, which may be substantially uniform along the entire length of distal portion 23, wherein second filamentary cross-sectional diameter d2 is smaller than first filamentary cross-sectional diameter $d_1$. (Intermediate portion 29 may uniformly taper in filamentary cross-sectional diameter from proximal portion 21 to distal portion 23.) Where, as in the present embodiment, proximal portion 21 of core-wire 13 has a greater filamentary cross-sectional diameter than does distal portion 23 of core-wire 13, a given tensioning force applied to core-wire 13 results in more stress being applied to distal portion 23 of core-wire 13 than to proximal portion 21 of core-wire 13. As a result, distal portion 23 experiences more strain, and hence greater elongation, than does proximal portion 21.

In the present embodiment, both proximal portion 21 of core-wire 13 and distal portion 23 of core-wire 13 may be generally circular in filamentary cross-sectional shape; however, it is to be understood that proximal portion 21 of core-wire 13 and distal portion 23 of core-wire 13 need not be circular in filamentary cross-sectional shape and may possess other filamentary cross-sectional shapes.

As noted above, in those embodiments in which core-wire 13 is a unitary wire made of a single material, different lengths of core-wire 13 may have different filamentary cross-sectional diameters. For example, proximal portion 21 and distal portion 23 may have different filamentary cross-sectional diameters from one another. The ratio of the filamentary cross-sectional diameters of proximal portion 21 and distal portion 23 of core-wire 13 may depend on the material properties of core-wire 13. The ratio may be selected such that a suitable differential strain can be achieved with only a modest exertion of force by an operator. The respective filamentary cross-sectional diameters of proximal portion 21 and distal portion 23 of core-wire 13 may be such that the tensile force applied by an operator will be insufficient for core-wire 13 to lose the memory of its remembered shape. In general, this means that the tensile force must be such that the distal section 23 is elongated by less than 8% of its relaxed length, and preferably within 2% to 7% of its relaxed length.

There exist a variety of methods for manufacturing a core-wire 13 having two or more portions that differ in their yield forces. In one method, a continuous wire made of a shaped-memory metal is ground to a smaller filamentary diameter to form the distal portion 23. The distal portion 23 is then heat-set to the desired shape. To achieve actuation of the core-wire 13, there must be a sufficient difference in the yield force of the proximal section 21 and the yield force of the distal section 23. This may be achieved by ensuring that the ratio of the filamentary diameter of the proximal section 21 to that of the distal section 23 is about 1.35 or greater. For a core-wire 13 having a non-circular cross-section, this may be achieved by ensuring that the ratio of the area of the proximal section 21 to that of the distal section 23 is about 1.8 or greater.

Figure 5:
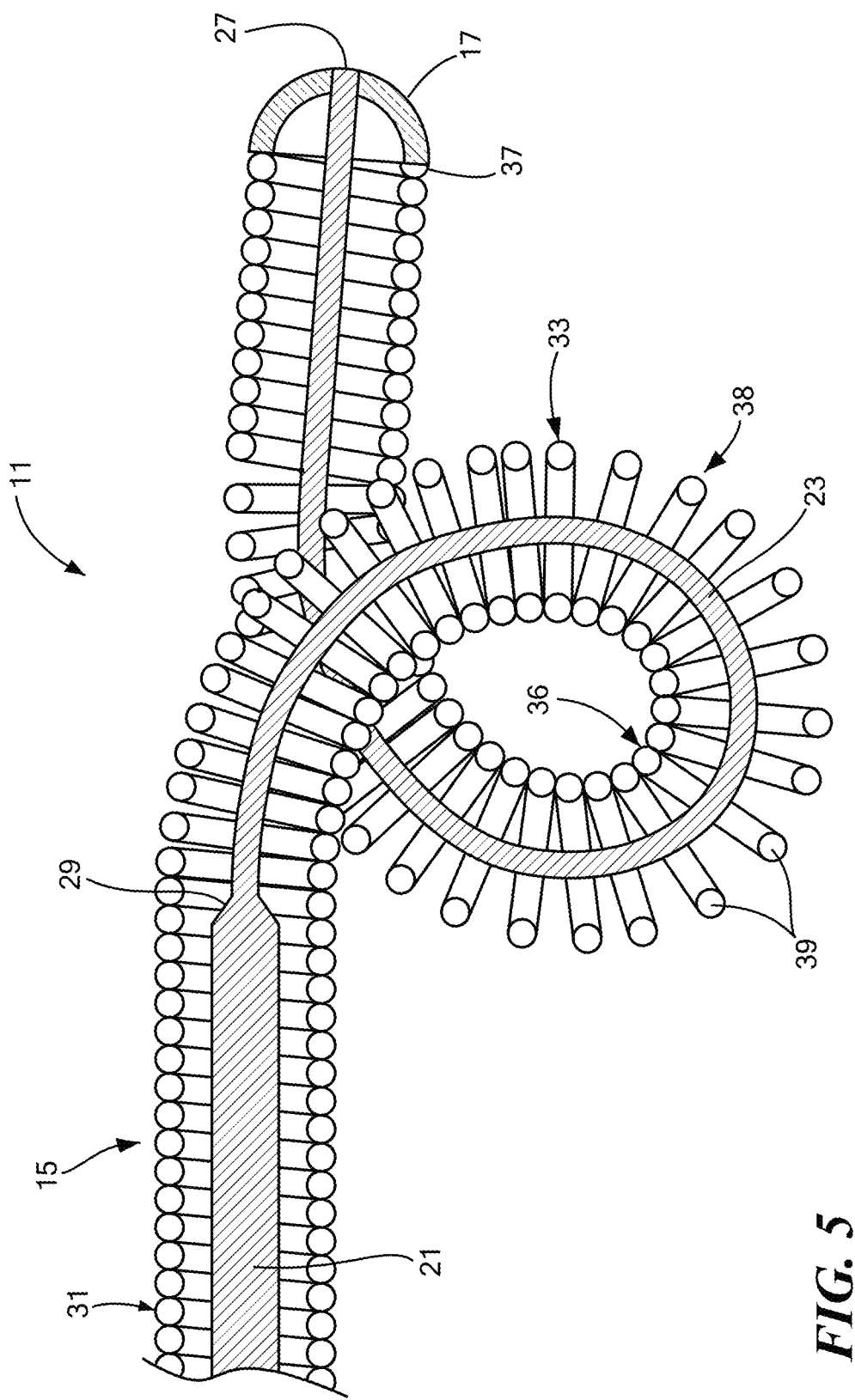
FIG. 5 is an enlarged fragmentary section view of a distal portion of the snare device of FIG. 1, the snare device being shown in its coiled state.
Figure 6:
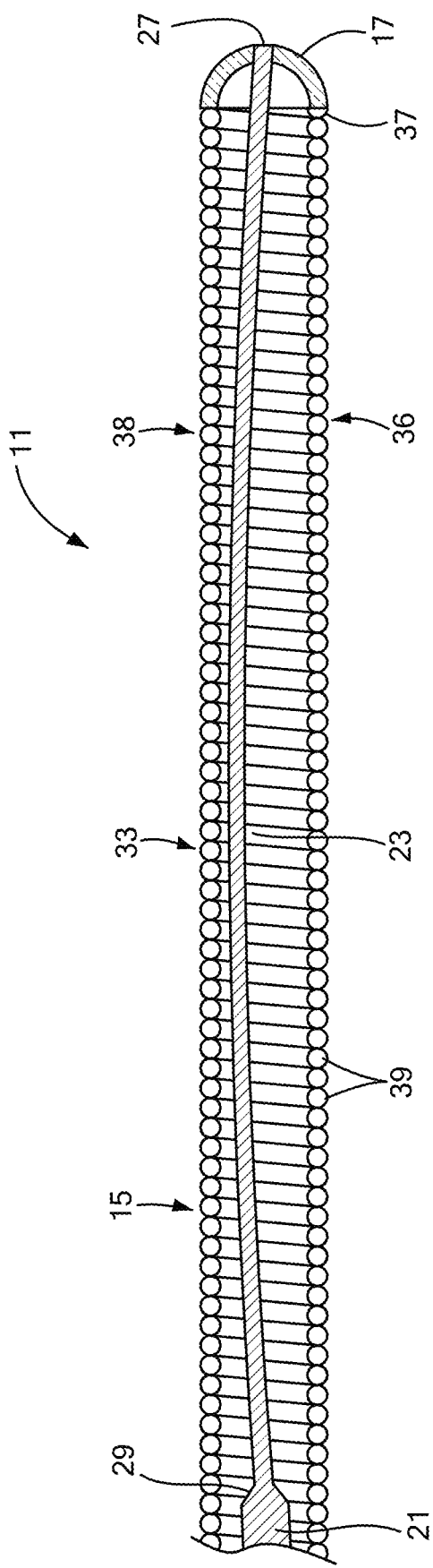
FIG. 6 is an enlarged fragmentary section view of a distal portion of the snare device of FIG. 1, the snare device being shown in its straightened state.

The actual transition from one state to another can be viewed as a wave traveling along core-wire 13. The direction in which this wave travels can be controlled by controlling the taper of the transition between proximal section 21 and distal section 23. In the case of a taper as shown in FIGS. 5 and 6, the wave travels from proximal section 21 to distal section 23 when the operator tensions on core-wire 13. Conversely, when the operator releases core-wire 13, the wave again travels from proximal section 21 to distal section 23.

Alternatively or additionally, core-wire 13 may be formed from a unitary length of material by a local heat-treatment to change the yield stress in the heat-treated region. This may be done, for example, by applying heat locally to the distal portion while masking the heat from the proximal portion. In some cases, the application of localized heat to form the distal section may eliminate a need to grind core-wire 13. In other cases, the application of localized heat may reduce the ratio of the proximal portion filamentary diameter to the distal portion filamentary diameter. Although, in the present embodiment, core-wire 13 may be a unitary structure, other methods exist of providing core-wire 13 with portions with different yield strengths. For example, core-wire 13 may be made by joining together two dissimilar materials having different yield strengths. More specifically, for example, core-wire 13 may be formed by joining together a proximal portion 21 made of stainless steel, MP35N® nickel-chromium-cobalt alloy (SPS Technologies LLC, Jenkintown, Pa.), or the like and a distal portion 23 made of NITINOL™ nickel-titanium alloy or the like. The aforementioned proximal and distal portions may be joined together by one or more of welding (e.g., butt, seam, lap, resistance, friction), soldering, brazing, or one or more adhesives.

Also, although core-wire 13 is described above as consisting of or comprising a super-elastic material, it is to be understood that core-wire 13 need not include a super-elastic material. For example, core-wire 13 may consist of or comprise a non-super-elastic material, such as a high tensile stainless steel, where distal portion 23 of core-wire 13 is significantly smaller in filamentary cross-sectional diameter than proximal portion 21 of core-wire 13 (e.g., filamentary cross-sectional diameter ratio of proximal portion 21 to distal portion 23 is greater than 3:1) and the strain/elongation of distal portion 23 does not exceed the yield point.

In addition, although not shown, core-wire 13 may be coated with a lubricious coating to reduce friction between core-wire 13 and support 15. An example of a composition or material that may be used to form the lubricious coating may be polytetrafluoroethylene (PTFE). The lubricious coating may be applied along the entire length of core-wire 13 or may be applied only to a portion thereof, for example, only to proximal portion 21. Alternatively and/or additionally, core-wire 13 may be coated with other types of materials, such as a hydrophilic and biocompatible composite material, examples of which include polyvinyl pyrrolidone (PVP), polyacrylamide, and hyaluronic acid.

Support 15, which is also shown separately in FIGS. 9 and 10, may be an elongated tubular structure of generally circular overall cross-section comprising a proximal portion 31 and a distal portion 33. In the present embodiment, support 15 may be in the form of a flexible coiled wire or filament. The coiled wire or filament of support 15 preferably has a round filamentary cross-sectional shape, such as a circular filamentary cross-sectional shape. A round filamentary cross-sectional shape is desirable as the edges of the round wire coil tend to line up more consistently when compressed, providing greater column strength when placed under compression.

As will be discussed further below, support 15 may be inserted over core-wire 13 so that proximal portion 31 may be generally disposed over much of proximal portion 21 of core-wire 13 and so that distal portion 33 may be generally disposed over much of distal portion 23 of core-wire 13.

Proximal portion 31 may terminate proximally at a proximal end 35 of support 15, and distal portion 33 may terminate distally at a distal end 37 of support 15. In the present embodiment, proximal portion 31 and distal portion 33 may be contiguous with one another, and support 15 may be a unitary or one-piece structure. (Alternatively, as disclosed, for example, in U.S. Pat. Nos. 6,500,185 and 6,652,536, support 15 may be a multi-piece structure wherein proximal portion 31 is a cannula and distal portion 33 is a coiled wire.) In the present embodiment, support 15 may have a uniform filamentary cross-sectional diameter d3 along its entire length, may have a uniform overall cross-sectional diameter d4 along its entire length, and may possess a uniform tensile strength along its entire length.

As noted above, support 15 may be a coiled wire and may comprise a segmented structure capable of articulation between its constituent segments or turns 39. Preferably, support 15 has an equilibrium compressed state, in which it defines a straight path corresponding to that shown in FIG. 2, and a non-equilibrium uncompressed state, in which proximal portion 31 follows a generally straight path and distal portion 33 follows a coiled path corresponding to that shown in FIG. 1. In the present embodiment, when support 15 is in its equilibrium compressed state, all or substantially all of turns 39 may be in contact with their neighboring turns

39. By contrast, when support 15 is in its non-equilibrium uncompressed state, turns 39 of distal portion 33 may be in contact with their neighboring turns 39 along an inner radius 36 but may be separated from one another along an outer radius 38. Thus, when support 15 is compressed, outer radius 38 may be comparatively shorter in length (and may be equal in length to inner radius 36) whereas, when support 15 is uncompressed, outer radius 38 may be comparatively longer in length (and may be longer in length than inner radius 36).

Support 15 may consist of or comprise a strong coilable material, such as a stainless steel, a titanium alloy, a chromium-cobalt alloy (e.g., MP35N® cobalt alloy, L-605 cobalt-chromium-tungsten-nickel alloy, etc.), or any other suitable strong coilable metal or other material. Support 15 may be made of one or more materials that are safe for use during magnetic resonance procedures. Support 15 may be coated with a hydrophilic and biocompatible composite material, such as polyvinyl pyrrolidone (PVP), polyacrylamide or hyaluronic acid. A suitable outer overall diameter of support 15 for general intra-vascular use may be approximately 0.014 inches.

To enable a surgeon to track the position of snare device 11 within a body, support 15 may be made of, or may include a portion made of, a radiopaque material such as platinum, tungsten, iridium, tin, gold, silver, or an alloy thereof. Alternatively, support 15 may be made of a coilable material coated with a radiopaque coating. Support 15 may comprise a close wound coil, with or without preload, or it may comprise an open wound coil.

In addition, although not shown, support 15 may further comprise a sleeve (or other type of cover) disposed around the outside of proximal portion 31 and/or a sleeve (or other type of cover) disposed around the outside of distal portion 33. Such sleeves may be, for example, a unitary structure covering both proximal portion 31 and distal portion 33. In some cases, a sleeve covering proximal portion 31 may be made of one or more materials possessing good lubricity, such as polytetrafluoroethylene (PTFE), or may be made of one or more materials, such as polyethylene terephthalate (PET) or urethane, to which a lubricious coating is applied. Alternatively and/or additionally, the sleeve may be coated with a hydrophilic and biocompatible composite material of the type discussed above in connection with core-wire 13 and support 15. In some cases, the sleeve may have properties conducive to protecting the coiled wire of support 15 from laser radiation (e.g., laser radiation from a YAG laser), which may be desirable where snare device 11 may be used in procedures involving the use of such lasers (e.g., stone lithotripsy). In some cases, a sleeve covering distal portion 33 may comprise materials having both highly elastic properties and low durometer, such as silicone or urethane, and/or may comprise materials having good lubricious properties, such as PTFE. Such a sleeve may serve to fill spaces between adjacent turns 39 of distal portion 33 of support 15 when snare device 11 is in its coiled state. By filling such spaces, snare device 11 may be better able to capture desired materials (e.g., stone fragments from lithotripsy, blood clots, foreign bodies) when in its coiled state. The sleeve, which may be attached to distal portion 33 of support 15, may have an inner diameter larger than the outer overall diameter of support 15, whereby snare device 11 in its coiled state may expand within the sleeve to create a channel suitable for restoring blood flow. The sleeve may be of a constant size or may be highly elastic and expandable or blood permeable. This arrangement may act as a temporary stent or an embolic protection device.

End cap 17, which is also shown separately in FIG. 11, may be a generally hemispherically-shaped member made of a rigid material, such as stainless steel or the like. In some cases, as in the present embodiment, end cap 17 may be hollow and may include an open bottom end 40-1 and an open top end 40-2. In other cases, as shown in other embodiments below, end cap 17 may be solid. End cap 17 may be used to mechanically couple core-wire 13 and support 15 at their respective distal ends. For example, in the present embodiment, distal end 27 of core-wire 13 may be fixed to bottom end 40-1 of end cap 17 by welding, soldering, brazing, or one or more epoxies or adhesives, and distal end 37 of support 15 may be fixed within open top end 40-2 of end cap 17 by welding, soldering, brazing, or one or more epoxies or adhesives.

Figure 12:
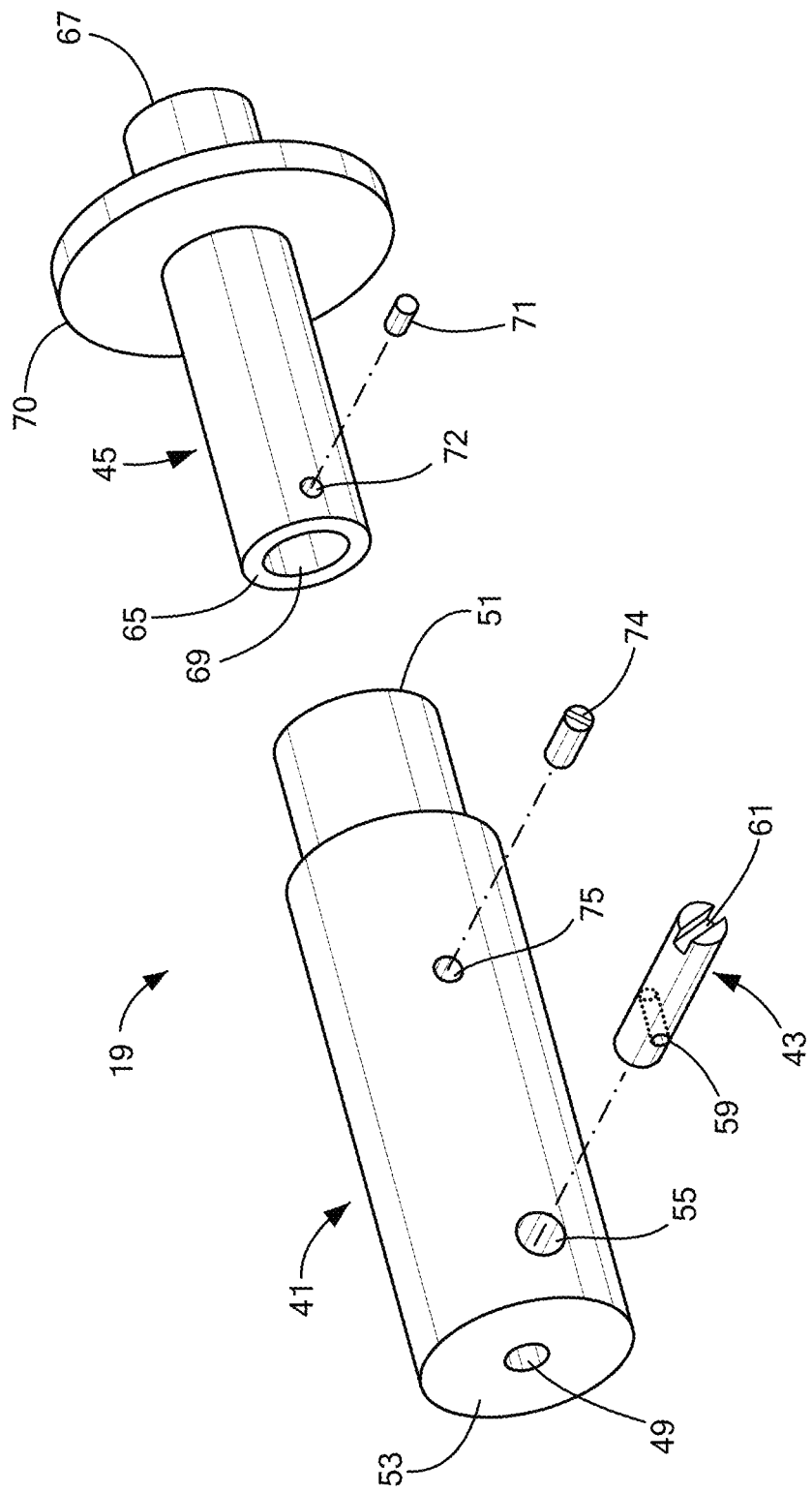
FIG. 12 is a partly exploded perspective view of the actuator shown in FIG. 1.

Actuator 19, which is also shown separately in FIG. 12, may comprise a handle 41, an anchor 43, and a slide 45.

Handle 41, which may be made of a rigid, durable material, such as a suitable polymer or metal, may be an elongated structure. In the present embodiment, handle 41 may be shaped to include a pair of longitudinally extending cavities, namely, a proximal cavity 47 and a distal cavity 49. Proximal cavity 47 may extend distally from a proximal end 51 of handle 41, and distal cavity 49 may extend proximally from a distal end 53 of handle 41. Proximal cavity 47 and distal cavity 49 may be axially aligned with one another and may be contiguous, whereby the distal end of proximal cavity 47 may open into the proximal end of distal cavity 49. In the present embodiment, proximal cavity 47 and distal cavity 49 may be generally cylindrical in cross-sectional shape, with proximal cavity 47 having a comparatively smaller diameter and with distal cavity 49 having a comparatively larger diameter. Proximal cavity 47 and distal cavity 49 may be appropriately dimensioned so that proximal portion 21 of core-wire 13 may be freely disposed therewithin.

Handle 41 may be shaped further to include a cavity 55. Cavity 55, which may be arranged to be transverse relative to the longitudinal axis of handle 41, may extend inwardly from a side 57 of handle 41 and may intersect with and pass through proximal cavity 47.

Anchor 43, which may be made of a rigid, durable material, such as a suitable polymer or metal, may be an elongated, barrel-shaped structure. Anchor 43 may be appropriately dimensioned to be snugly mounted, yet rotatably adjustable, within cavity 55 of handle 41. A transverse channel 59 may be provided in anchor 43 so that proximal end 25 of core-wire 13 may be secured to anchor 43 (for example, by being inserted through channel 59 and then tied around anchor 43). A slot 61 may be provided in an outer end of anchor 43 and may be shaped to receive a flat-head screwdriver or similarly shaped tool (not shown) that may be used to rotate anchor 43 within cavity 55. As can be appreciated, by rotating anchor 43 within cavity 55, the amount of tension that is applied to core-wire 13 may be adjusted.

Slide 45, which may be made of a rigid, durable material, such as a suitable polymer or metal, may be an elongated, hollow structure. Slide 45 may be appropriately dimensioned to be slidably mounted within distal cavity 49 of handle 41 so as to move proximally and distally therewithin. Slide 45 may be shaped to include a proximal end 65, a distal end 67, and a longitudinal cavity 69 that may extend from proximal end 65 to distal end 67. Cavity 69 may be appropriately dimensioned to permit core-wire 13 to extend freely therethrough. Proximal end 35 of support 15 may be fixedly secured to distal end 67 of slide 45 by welding, soldering, brazing, adhesive or other suitable means. A grip 70 may be fixedly mounted on slide 45 for use in moving slide 45 back and forth within handle 41. A stop 71 may be mounted in an opening 72 on slide 45 and may be movable within a track 73 formed in handle 41. Stop 71 may be arranged for contact with a set screw 74 mounted in an opening 75 on handle 41 to define a range of movement of slide 45 back and forth relative to handle 41.

To summarize, in the present embodiment, proximal end 25 of core-wire 13 may be secured to anchor 43, which, in turn, may be coupled to handle 41, and distal end 27 of core-wire 13 may be secured to end cap 19. Proximal end 35 of support 15 may be secured to slide 45, which, in turn, may be slidably mounted on handle 41, and distal end 37 of support 15 may be secured to end cap 19. Alternatively stated, proximal end 35 of support 15 may be movable proximally and distally relative to proximal end 25 of core-wire 13 whereas distal end 25 of core-wire 13 may be fixed relative to distal end 35 of support 15.

In view of the above, when slide 45 is at its most proximal position, proximal end 35 of support 15 is also at its most proximal position. As a result, the compressive force applied to support 15 is at its relative minimum, and, consequently, a distally-directed force applied to distal end 37 of support 15 is also at its relative minimum. In addition, due to the coupling of core-wire 13 and support 15 at end cap 19, the distally-directed tensioning force applied to distal end 27 of core-wire 13 is also at its relative minimum. With the tensioning of core-wire 13 thus at its relative minimum, core-wire 13 assumes its relaxed state, with distal portion 23 of core-wire 13 forming a looped or coiled shape. With core-wire 13 assuming a looped or coiled shape, distal section 33 of support 15, which is constrained to follow the shape of distal section 23 of core-wire 13, assumes a correspondingly looped or coiled shape. While in this looped or coiled shape, distal section 33 of support 15 is uncompressed.

By contrast, when slide 45 is at its most distal position, proximal end 35 of support 15 is also at its most distal position. As a result, the compressive force applied to support 15 is at its relative maximum, and, consequently, the distally-directed force applied to distal end 37 of support 15 is also at its relative maximum. In addition, due to the coupling of core-wire 13 and support 15 at end cap 19, the distally-directed tensioning force applied to distal end 27 of core-wire 13 is also at its relative maximum. With the tensioning of core-wire 13 thus at its relative maximum, core-wire 13 stretches, particularly distal portion 23 of core-wire 13. As distal portion 23 of core-wire 13 stretches, it straightens. In this straightened state, core-wire 13 no longer forces support 15 to adopt a looped or coiled shape. As a result, distal section 33 of support 15 is allowed to revert to its equilibrium compressed state in which it follows a straight path. Thus, the movement of slide 45 from its proximal position to its distal position serves both to apply a tensile force to core-wire 13 and to apply a compressive force to the support 15, the tensile force causing core-wire 13 to transition from its relaxed state to its tensioned state, the compressive force causing support 15 to transition from its uncompressed state to its compressed state. When support 15 is in its compressed state and follows a straight path, core-wire 13 is largely constrained by support 15 to follow a generally straight path, despite exhibiting some minor degree of flexure or undulation within support 15 (see FIG. 6).

In use, snare device 11 may be transformed from its coiled state to its straightened state by moving slide 45 from its most proximal position to its most distal position. With snare device 11 thus transformed to its straightened state, snare device 11 may then be inserted into a patient to a desired location, such as to a location where end cap 17 of snare device 11 may be positioned to a point just beyond an object to be snared. Then, snare device 11 may be transformed back to coiled state from its straightened state by moving slide 45 back to its most proximal position from its most distal position, whereby the object may be snared by the coiled or looped portion of snare device 11. Because of its coiled or looped shape, snare device 11 may be particularly well-suited for grasping a medical instrument to guide it to a desired location. For example, snare device 11 could be inserted through an implanted abdominal aortic aneurysm (AAA) endovascular aneurysm repair (EVAR) stent into the second iliac artery and adjacent to a guidewire that has been placed in the femoral artery. Deploying the circular or looped shape around the aforementioned guidewire to ensnare it, snare device 11 could then be withdrawn to guide the guidewire into the EVAR stent. Other possible uses for snare device 11 may be found in U.S. Pat. Nos. 6,500,185 and 6,652,536.

Figure 13:
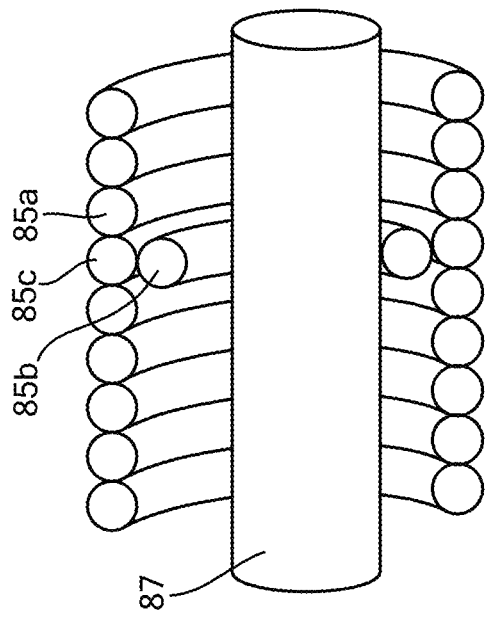
FIG. 13 is a cross-section of a conventional snare device having a permanently skewed turn of its coiled wire support.

As noted above, as support 15 transitions from its uncompressed state to its compressed state, turns 39 of support 15 may experience varying radial forces. These forces may cause one or more turns 39 to become radially displaced or "skewed" relative to core-wire 13. If the radial displacement is not too large, support 15 will not contact core-wire 13, and the tension within support 15 will restore the radially displaced turns 39 to their equilibrium aligned positions upon removal of the radial force. However, as shown in FIG. 13, if the radial displacement is too large, as may be the case for a snare device like snare device 10 of U.S. Pat. No. 6,500,185, normally non-neighboring turns 85$a$ and 85$c$ may be caused to become adjacent to one another, permanently misaligning an intervening turn 85$b$. If the permanently misaligned turn 85$b$ extends far enough inwardly to contact core-wire 87, core-wire 87 may be impaired from straightening.

In accordance with the present invention, it has unexpectedly been found that the aforementioned problem of skewing may be ameliorated if distal portion 33 of support 15 and distal portion 23 of core-wire 13 are characterized by the following relationship:

Break Load$_{(distal\ portion\ 33\ of\ support\ 15)}$>Plateau Force$_{(distal\ portion\ 23\ of\ core-wire\ 13)}$ wherein the break load of distal portion 33 of support 15 is equal to the tensile strength of distal portion 33 of support 15 multiplied by the filamentary cross-sectional area of distal portion 33 of support 15, wherein distal portion 23 of core-wire 13 has a filamentary cross-sectional area and also has an upper plateau stress in response to a tensile force applied thereto, and wherein the plateau force of distal portion 23 of core-wire 13 is equal to the upper plateau stress multiplied by the cross-sectional area of distal portion 23 of core-wire 13. To ensure that skewing does not occur anywhere along the length of distal portion 33 of support 15, the foregoing relationship (i.e., the break load of distal portion 33 of support 15 is greater than the plateau force of distal portion 23 of core-wire 13) should apply to the entire length of distal portion 33 of support 15.

As an example of the foregoing relationship, distal portion 33 of support 15 may have a tensile strength of 322,000 psi and a filamentary cross-sectional area of 9.62×10$^{-6}$in$^2$, and distal portion 23 of core-wire 13 may have a filamentary cross-sectional area of 3.28×10$^{-5}$in$^2$ and an upper plateau stress of 81,000 psi. As a result, the break load of distal portion 33 of support 15 is 3.10 (i.e., 322,000 psi times $9.62 \times 10^{-6}$ in$^2$), which is greater than the plateau force of 2.66 (i.e., 81,000 psi times $3.28 \times 10^{-5}$ in$^2$) for distal portion 23 of core-wire 13.

It is to be understood that the above values are merely illustrative and that, as long as the break load of distal portion 33 of support 15 is greater than the plateau force of distal portion 23 of core-wire 13, the tensile strength of distal portion 33 of support 15, the filamentary cross-sectional area of distal portion 33 of support 15, the filamentary cross-sectional area of distal portion 23 of core-wire 13, and the plateau stress of distal portion 23 of core-wire 13 may fall anywhere within broad ranges of values. For example, and without limitation, the tensile strength of distal portion 33 of support 15 may be 300,000-420,000 psi, the filamentary cross-sectional area of distal portion 33 of support 15 may be $4.91 \times 10^{-6} - 1.06 \times 10^{-4}$ in$^2$, the filamentary cross-sectional area of distal portion 23 of core-wire 13 may be $1.80 \times 10^{-5} - 4.13 \times 10^{-4}$ in$^2$, and the upper plateau stress of distal portion 23 of core-wire 13 may be 70,000-90,000 psi. Additional examples falling within these ranges are presented below.

By comparison, if the plateau force for the distal portion of the core-wire is greater than the break load of the distal portion of the support coil, the support coil may be expected to skew. For example, if the distal portion of the core-wire were to have an upper plateau stress of 84,000 psi and a filamentary cross-sectional area of $2.04 \times 10^{-5}$ in$^2$ and if the support coil were to consist of a platinum alloy filament having a maximum ultimate tensile strength of about 180,000 psi and a filamentary cross-sectional area of $4.91 \times 10^{-6}$ in$^2$, the support coil may be expected to skew when the snare device is straightened by tensioning the core-wire and compressing the support coil. This is because the plateau force of the distal portion of the core-wire would be 1.72 lbs, which would be greater than the break force of 0.88 lbs for the support coil. In a similar fashion, if the distal portion of the core-wire were to have an upper plateau stress of 84,000 psi and a filamentary cross-sectional area of $2.04 \times 10^{-5}$ in$^{-2}$ and if the support coil were to consist of a stainless steel wire filament having a maximum ultimate tensile strength of about 340,000 psi and a filamentary cross-sectional area of $4.91 \times 10'$ in$^2$, the support coil may be expected to skew when the snare device is straightened by tensioning the core-wire and compressing the support coil. This is because the plateau force of the distal portion of the core-wire would be 1.72 lbs, which would be greater than the break force of 1.67 lbs for the support coil.

Also, as alluded to above in connection with the '638 publication, if the support coil has a rectangular filamentary cross-section, the support coil may be expected to skew. This is because the present inventor believes that a rectangular cross-sectional shape of the support coil will permit variable alignment at the support coil edges.

Another important aspect of the design of the snare device of the present invention is that the distal portion of the core-wire have a reasonably uniform filamentary diameter over its entire length in its relaxed state. For example, where a continuous wire that is made of a shaped-memory metal is ground to a smaller filamentary diameter to form the distal portion of the core-wire, the filamentary diameter of the distal portion of the core-wire should be reasonably uniform over its entire length. A typical barrel grind tolerance of ±0.0002 inch is reasonable for diameters larger than 0.003 inch. If the distal grind diameter were to decrease substantially as one moves distally along the distal portion of the core-wire, the tensile force associated with the loading plateau required to overcome the larger, more proximal diameter would result in the smaller diameter exceeding its loading plateau and elongating beyond the 8% recoverable strain. As a result, the smaller diameter would be plastically deformed and elongated, and the device would lose its shape in the relaxed position.

On the other hand, if the distal grind diameter were to increase substantially as one moves distally along the distal portion of the core-wire, the mechanism would not be able to transition completely from the relaxed state to the tensioned/compressed state. The tensile force that would be required to overcome the larger diameter would also elongate the unground core-wire, resulting in hysteresis along the entire length. Moreover, the extended length of the core-wire would prevent the support from ever being fully compressed, and the handle stroke would be insufficient to accommodate this movement.

Another aspect of the design of the snare device of the present invention is the curvature of core-wire 13. It is generally known that NITINOL™ nickel-titanium alloy has a largely recoverable engineering strain, e, of 6-8%. Experimentally, the NITINOL™ core-wire is heat-set to 9% strain, according to the equation $e = 1/(2R/t + 1)$, where R equals the bend radius and t equals the wire thickness. Because a straight configuration of the device is defined by the compressed coil, the core-wire does not have to be completely straight when placed under tension and, instead, may have residual bends even when the device is straight (see FIG. 6). However, if the NITINOL™ core-wire has any sharp bends, the device will tend to skew in these locations since the compression force to overcome the tensioned wire shape will be focused at these points. Skewing from sharp bends may be mitigated against by increasing the ratio of coil wire break load vs core-wire plateau force.

Figure 14:
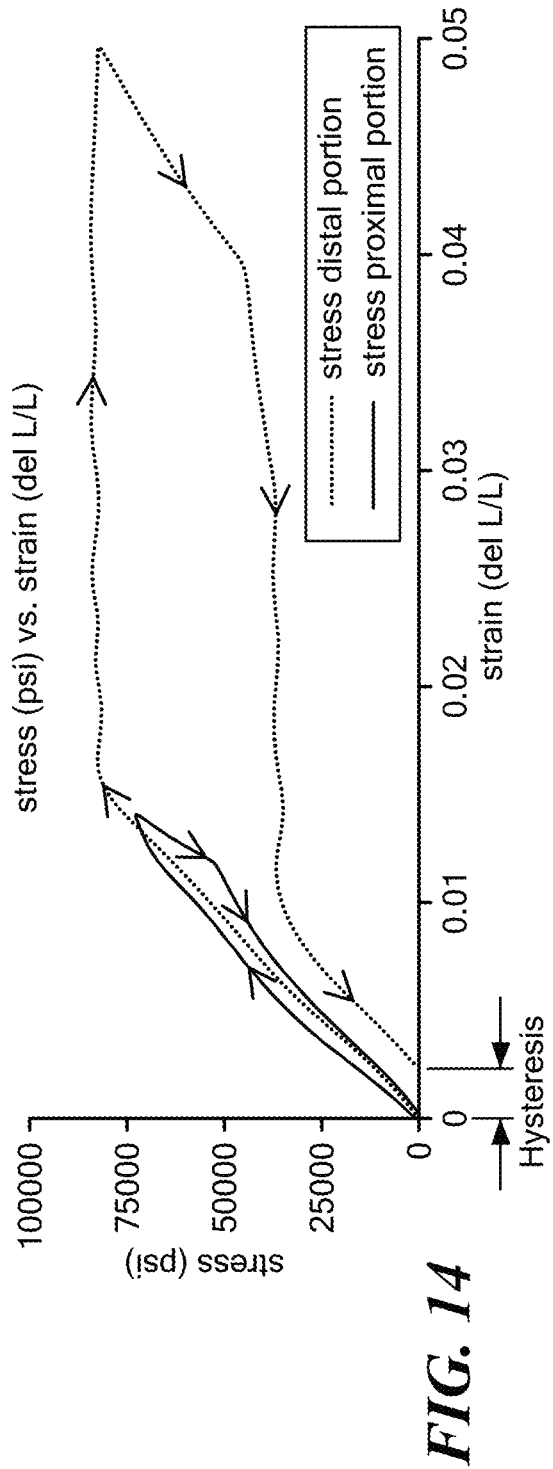
FIG. 14 is a graphic representation of a stress-strain curve for a core-wire like that shown in FIG. 5.

Referring now to FIG. 14, there is graphically shown a stress-strain curve for an embodiment of core-wire 13 in which core-wire 13 is made of NITINOL™ nickel-titanium alloy, proximal portion 21 is circular in cross-sectional shape and has a uniform filamentary cross-sectional diameter of 0.012 in, and distal portion 23 is circular in cross-sectional shape and has a uniform filamentary cross-sectional diameter of 0.0079 in. As can be seen from the aforementioned stress-strain curve, distal portion 23 exhibits an upper plateau stress (i.e., an upper region of approximately constant stress in the stress-strain curve) of approximately 82,000-84,000 psi.

Figure 15:
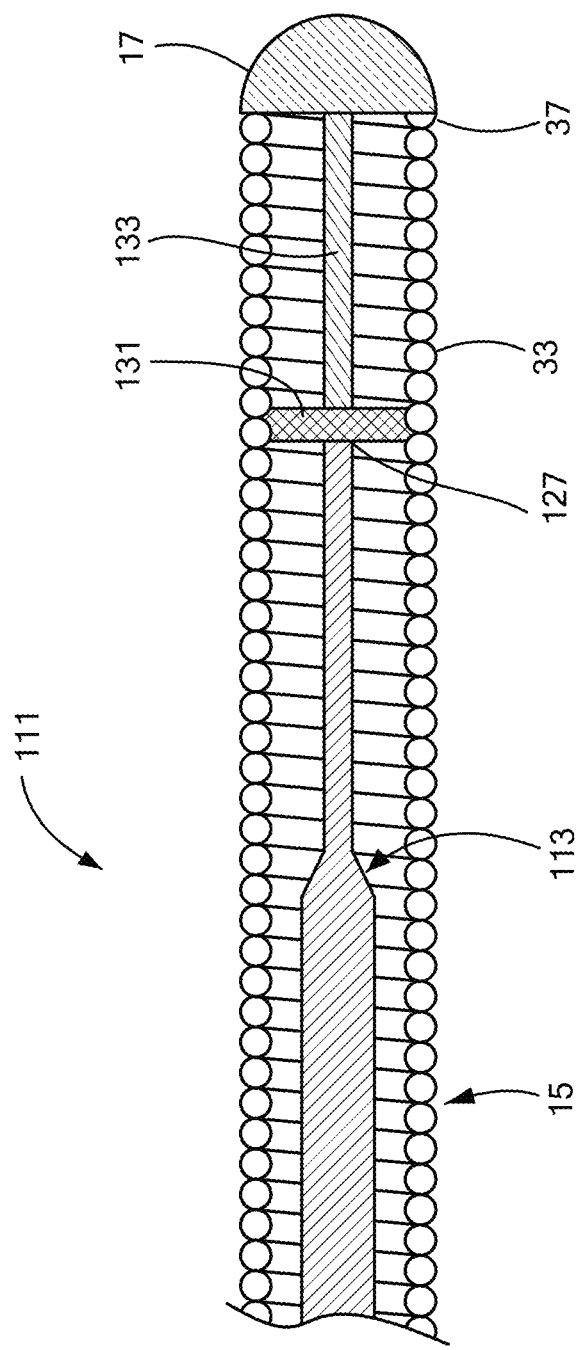
FIG. 15 is an enlarged fragmentary section view of a second embodiment of a snare device constructed according to the teachings of the present invention, the snare device being shown in a straightened state.

Referring now to FIG. 15, there is shown an enlarged fragmentary section view of a second embodiment of a snare device constructed according to the teachings of the present invention, the snare device being represented generally by reference numeral 111. Details of snare device 111 that are discussed elsewhere in this application or that are not critical to an understanding of the invention may be omitted from FIG. 15 and/or from the accompanying description herein or may be shown in FIG. 15 and/or described herein in a simplified manner.

Snare device 111 may be similar in most respects to snare device 11. One difference between snare device 111 and snare device 11 may be that, whereas snare device 11 may comprise a core-wire 13 whose distal end 27 is anchored to end cap 17, snare device 111 may comprise a core-wire 113 whose distal end 127 is not anchored to end cap 17. Instead, distal end 127 of core-wire 113 may be anchored to an anchoring element 131 disposed on distal portion 33 of support 15 at an intermediate point that is distal to the coiled or looped shape of core-wire 113 and is proximal to distal end 37 of support 15. A safety wire 133 may extend distally from anchoring element 131 to end cap 17 to prevent the support 15 from unravelling. This arrangement isolates any tensile force applied to core-wire 113 to points proximal to the aforementioned intermediate point and results in a coiled or looped shape having a floppy and atraumatic distal tip. Such an atraumatic tip may be advantageous because it enables the instrument to be maneuvered in constricted regions without a significant risk of perforating or otherwise damaging surrounding structures.

Figure 16:
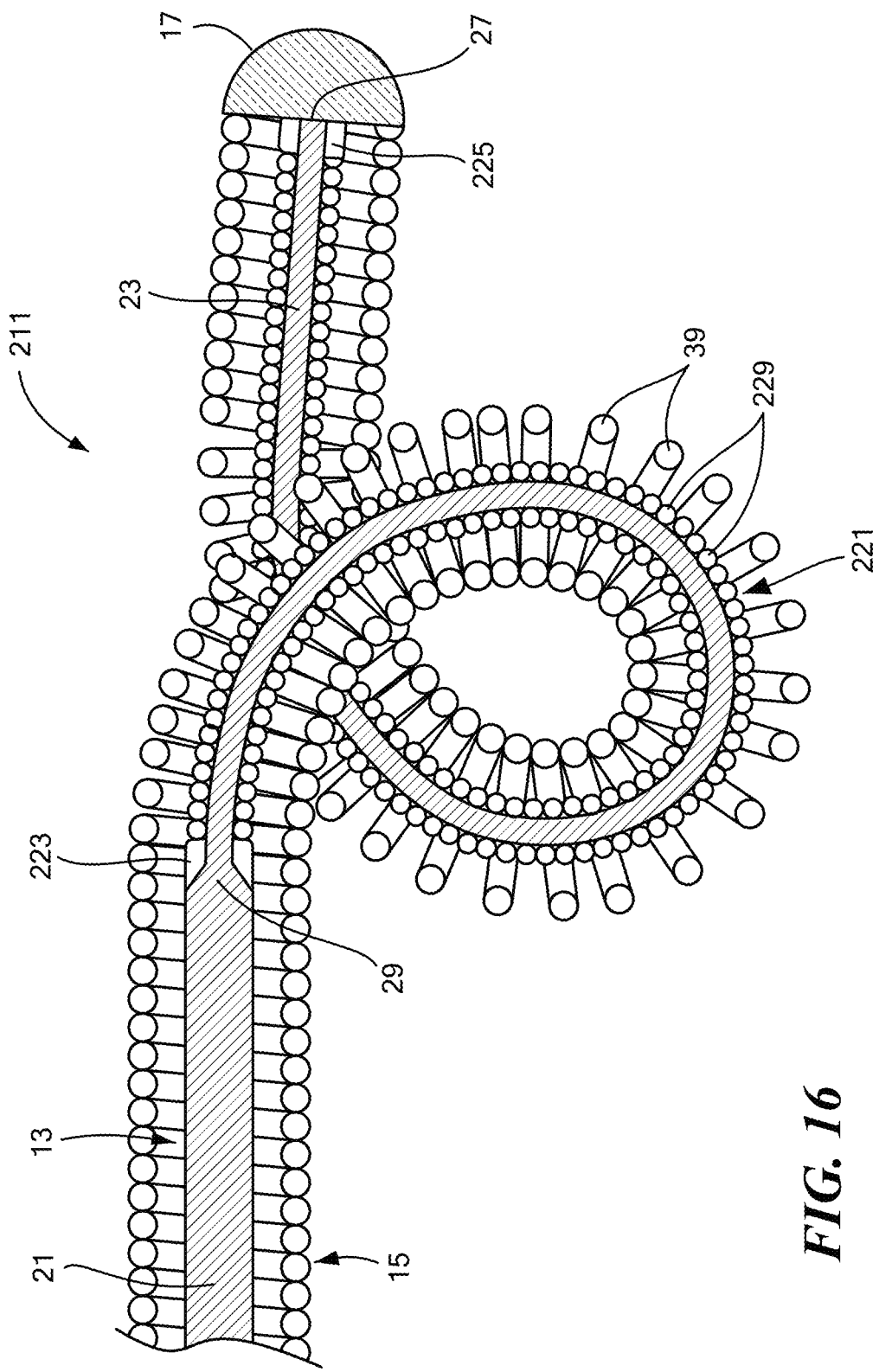
FIG. 16 is an enlarged fragmentary section view of a third embodiment of a snare device constructed according to the teachings of the present invention, the snare device being shown in a coiled state.

Referring now to FIG. 16, there is shown an enlarged fragmentary section view of a third embodiment of a snare device constructed according to the teachings of the present invention, the snare device being represented generally by reference numeral 211. Details of snare device 211 that are discussed elsewhere in this application or that are not critical to an understanding of the invention may be omitted from FIG. 16 and/or from the accompanying description herein or may be shown in FIG. 16 and/or described herein in a simplified manner.

Snare device 211 may be similar in most respects to snare device 11. One difference between snare device 211 and snare device 11 may be that snare device 211 may further comprise a spacer coil 221. Spacer coil 221 may have a proximal end attached to a proximal spacer 223 mounted on intermediate portion 29 of core-wire 13 and may have a distal end attached to a distal spacer 225 mounted on core-wire 13 proximate to distal end 27. Spacer coil 221 may comprise or consist of a radiopaque material, such as platinum. However, other materials may also be used depending on the specific application of the instrument 211. Other tubular structures may be used in place of spacer coil 221 to enclose core-wire 13. For example, baffles, bellows or any such flexible and compressible tube having dimensions as described below can also be used. Spacer coil 221 may consist of a single wire formed into a coil or may comprise two or more wires formed into a coil.

Spacer coil 221 may be in contact with core-wire 13 or may be separated therefrom by a clearance that is small enough to prevent articulating spacer-coil segments or turns 229 of spacer coil 221 from, themselves, becoming radially displaced relative to core-wire 13. This clearance is preferably determined by the dimensions of spacer coil 221. In one embodiment, the clearance is selected to be less than the radius of the windings or turns that make up spacer coil 221.

In addition, spacer coil 221 and support 15 may be dimensioned relative to one another to minimize the skewing of support 15 and, additionally, to prevent spacer coil 221 and support 15 from binding with each other during use. To minimize the likelihood that turns of support 15 may protrude into openings formed between turns of spacer coil 221, the pitch angle of turns 229 of spacer coil 221 is preferably selected to be different from the pitch angle of turns 39 of support 15. Such a difference can be achieved by winding spacer coil 221 and support 15 in opposite directions. In one embodiment, these two pitch angles are at right angles to each other. However, any difference in pitch angle will reduce the likelihood of penetration.

Figure 17:
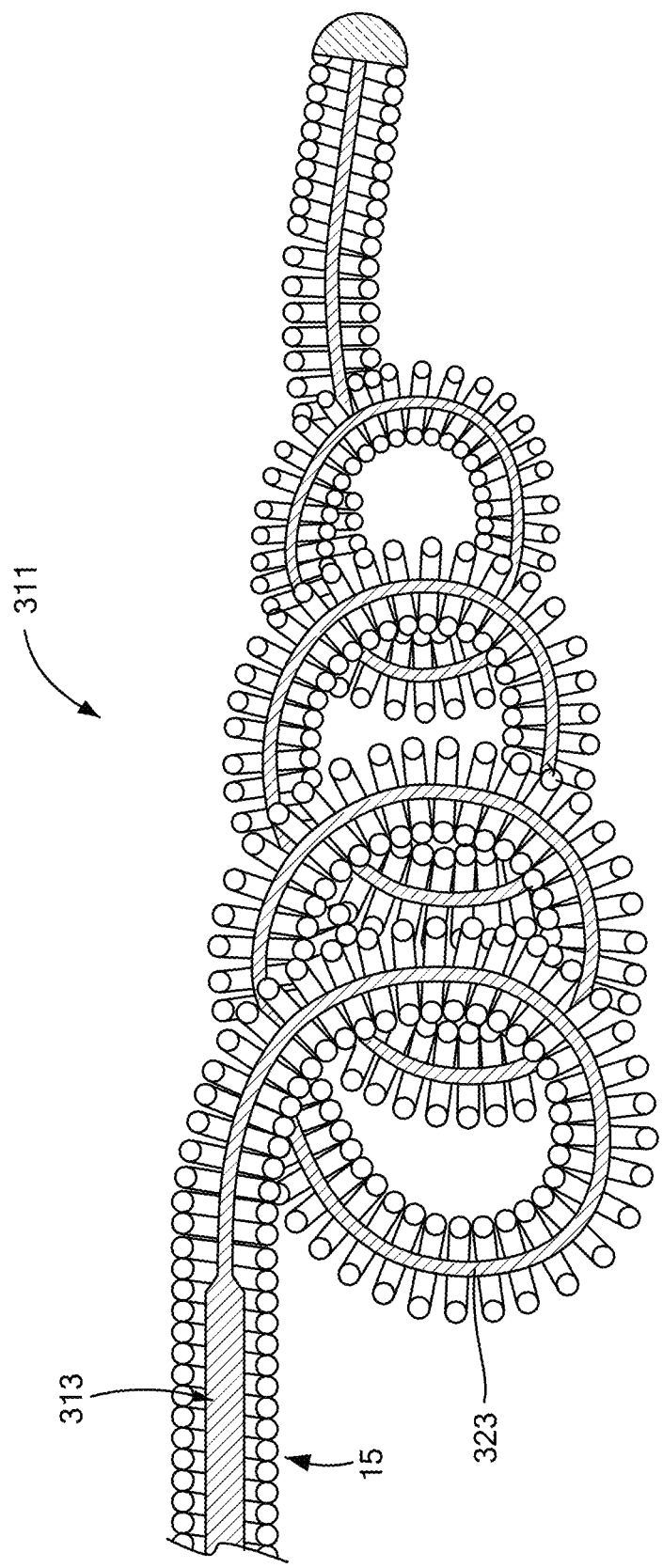
FIG. 17 is an enlarged fragmentary section view of a fourth embodiment of a snare device constructed according to the teachings of the present invention, the snare device being shown in a coiled state.

Referring now to FIG. 17, there is shown an enlarged fragmentary section view of a fourth embodiment of a snare device constructed according to the teachings of the present invention, the snare device being represented generally by reference numeral 311. Details of snare device 311 that are discussed elsewhere in this application or that are not critical to an understanding of the invention may be omitted from FIG. 17 and/or from the accompanying description herein or may be shown in FIG. 17 and/or described herein in a simplified manner.

Snare device 311 may be similar in most respects to snare device 11. One difference between snare device 311 and snare device 11 may be that snare device 311 may comprise a core-wire 313, instead of core-wire 13. Core-wire 313 may differ from core-wire 13 in that core-wire 313 may comprise a distal portion 323 that may include a conical helix (i.e., larger turns proximally and tapering smaller turns distally) when in its relaxed state. Such a conical helix may be used like a basket and may be useful for such purposes as capturing kidney stone fragments during lithotripsy (retropulsion). Although not shown, a blood permeable sack or sock (such as in U.S. Patent Application Publication No. 2009/0209987 A1) may be attached to the distal region 35 of support 15 to enable device 311 to be used as an embolic protection device.

Figure 18:
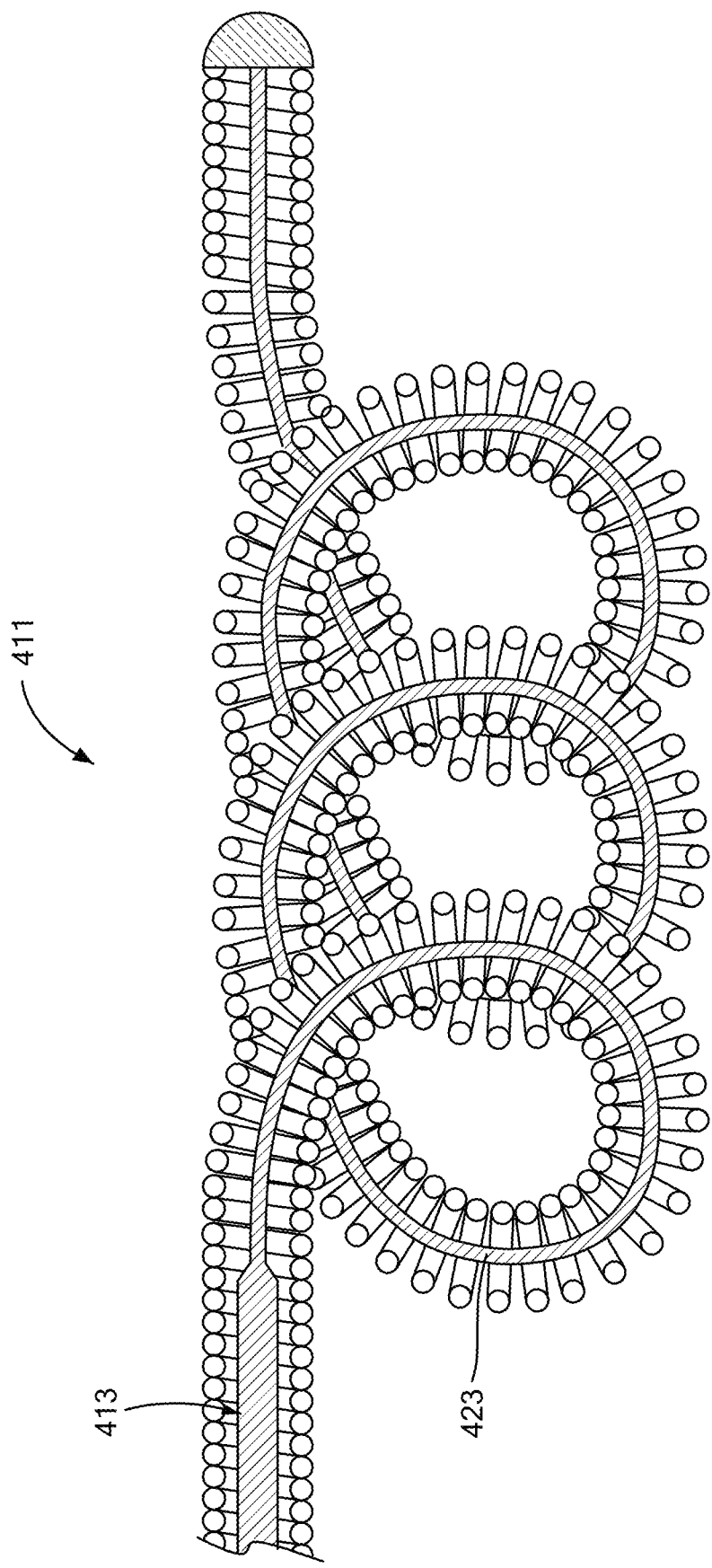
FIG. 18 is an enlarged fragmentary section view of a fifth embodiment of a snare device constructed according to the teachings of the present invention, the snare device being shown in a coiled state.

Referring now to FIG. 18, there is shown an enlarged fragmentary section view of a fifth embodiment of a snare device constructed according to the teachings of the present invention, the snare device being represented generally by reference numeral 411. Details of snare device 411 that are discussed elsewhere in this application or that are not critical to an understanding of the invention may be omitted from FIG. 18 and/or from the accompanying description herein or may be shown in FIG. 18 and/or described herein in a simplified manner.

Snare device 411 may be similar in most respects to snare device 11. One difference between snare device 411 and snare device 11 may be that snare device 411 may comprise a core-wire 413, instead of core-wire 13. Core-wire 413 may differ from core-wire 13 in that core-wire 413 may comprise a distal portion 423 that may include a cylindrical helix when in its relaxed state. Such a cylindrical helix may be useful for such purposes as forming a temporary stent to open an otherwise occluded or constricted lumen in a person's body. For example, snare device 411 could be used to open blood vessels to restore blood flow, to open gastrointestinal vessels to allow the flow of food, bile, etc., and to open a ureter to restore the flow of urine.

Figure 19:
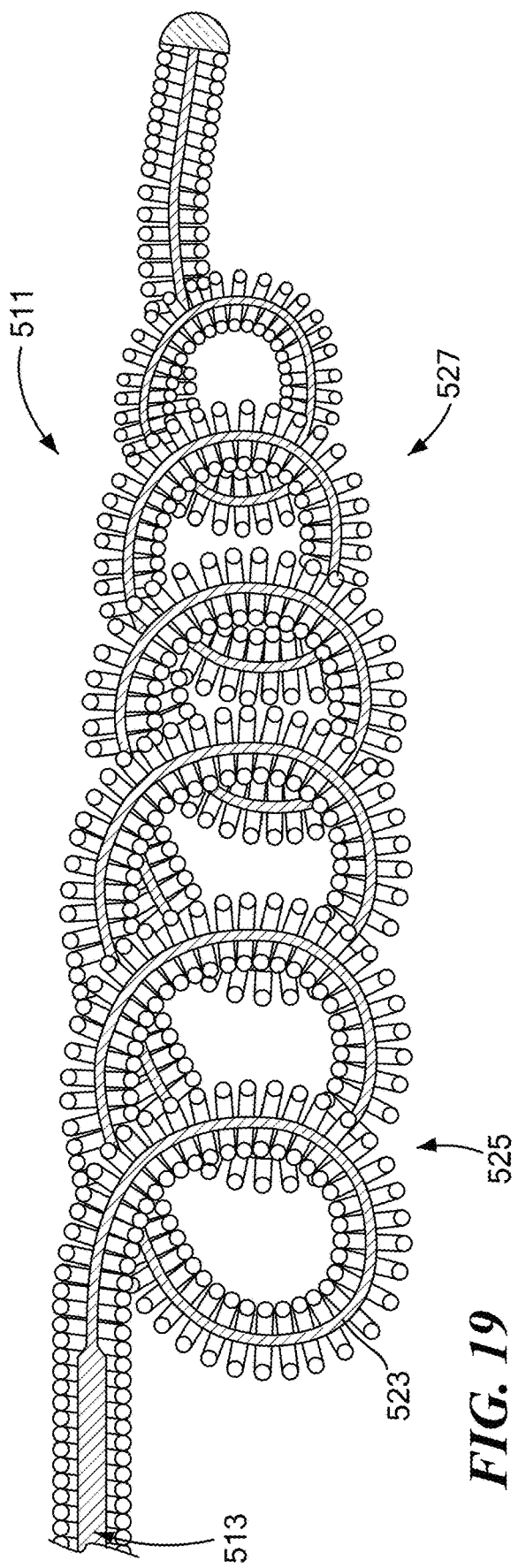
FIG. 19 is an enlarged fragmentary section view of a sixth embodiment of a snare device constructed according to the teachings of the present invention, the snare device being shown in a coiled state.

Referring now to FIG. 19, there is shown an enlarged fragmentary section view of a sixth embodiment of a snare device constructed according to the teachings of the present invention, the snare device being represented generally by reference numeral 511. Details of snare device 511 that are discussed elsewhere in this application or that are not critical to an understanding of the invention may be omitted from FIG. 19 and/or from the accompanying description herein or may be shown in FIG. 19 and/or described herein in a simplified manner.

Snare device 511 may be similar in most respects to snare device 11. One difference between snare device 511 and snare device 11 may be that snare device 511 may comprise a core-wire 513, instead of core-wire 13. Core-wire 513 may differ from core-wire 13 in that core-wire 513 may comprise a distal portion 523 that may include, when in its relaxed state, a combination of a proximal cylindrical helix 525 and a distal cone 527. Such a shape may be useful as a snare to capture objects, such as blood clots, gallstones, and other foreign bodies.

The following examples are provided for illustrative purposes only and are in no way intended to limit the scope of the present invention:

EXAMPLE 1

A snare device like that of FIGS. 1-6 of the present application was constructed. The core-wire of the snare device was made of NITINOL™ nickel-titanium alloy, with the proximal portion of the core-wire being circular in cross-sectional shape and having a uniform filamentary cross-sectional diameter of 0.0075 in and with the distal portion of the core-wire being circular in cross-sectional shape and having a uniform filamentary cross-sectional diameter of 0.0051 in. Consequently, the filamentary cross-sectional area of the distal portion of the core-wire was $2.04 \times 10^{-5}$ in$^2$. The upper plateau stress for the distal portion of the core-wire was 84,000 psi. As a result, the plateau force for the distal portion of the core-wire was 1.72 lbs.

The support of the subject snare device was in the form of a coil made of a stainless steel wire of round cross-section having the highest tensile strength that is commercially available, i.e., 420,000 psi (Fort Wayne Metals, Fort Wayne, Indiana). The support had a uniform overall outer diameter of 0.0135 in and a uniform overall inner diameter of 0.0085 in. Consequently, the filamentary cross-sectional diameter of the support was 0.0025 in, and the filamentary cross-sectional area of the support was $4.91 \times 10^{-6}$ in$^2$. As noted above, the ultimate tensile strength of the support was 420,000 psi. As a result, the break force for the support was 2.06 lbs, which is greater than the plateau force of 1.72 lbs. Table 1 below summarizes some of the above-noted values.

TABLE 1

| Core-wire | | | | Support | | | |
|---|---|---|---|---|---|---|---|
| Distal Portion Diameter (in) | Distal Portion Cross-Sectional Area (in$^2$) | Distal Portion Upper Plateau Stress (psi) | Distal Portion Plateau Force (lbs) | Filamentary Diameter (in) | Cross-Sectional Area (in$^2$) | Ultimate Tensile Strength (psi) | Break Force (lbs) |
| 0.0051 | $2.04 \times 10^{-5}$ | 84,000 | 1.72 | 0.0025 | $4.91 \times 10^{-6}$ | 420,000 | 2.06 |

For the above-described embodiment, the support coil column strength was found to be sufficient to resist skewing when compressed by the tensile force applied by the core-wire.

EXAMPLE 2

A snare device similar to that of Example 1, but larger in diameter, was constructed. The core-wire of the snare device was made of NITINOL™ nickel-titanium alloy, with the proximal portion of the core-wire having a uniform filamentary cross-sectional diameter of 0.0121 in and with the distal portion of the core-wire having a uniform filamentary cross-sectional diameter of 0.0082 in. Consequently, the filamentary cross-sectional area of the distal portion of the core-wire was $5.28 \times 10^{-5}$ in'. The upper plateau stress for the distal portion of the core-wire was 85,000 psi. As a result, the plateau force for the distal portion of the core-wire was 4.5 lbs.

The support of the subject snare device was in the form of a coil made of a stainless steel wire of round cross-section having an ultimate tensile strength of 340,000 psi. The support had a uniform overall outer diameter of 0.0226 in and a uniform overall inner diameter of 0.0136 in. Consequently, the filamentary cross-sectional diameter of the support was 0.0045 in, and the filamentary cross-sectional area of the support was $1.59 \times 10^{-5}$ in$^2$. As noted above, the ultimate tensile strength of the support was 340,000 psi. As a result, the break force for the support was 5.4 lbs, which is greater than the plateau force of 4.5 lbs. Table 2 below summarizes some of the above-noted values.

TABLE 2

| Core-wire | | | | Support | | | |
|---|---|---|---|---|---|---|---|
| Distal Portion Diameter (in) | Distal Portion Cross-Sectional Area (in$^2$) | Distal Portion Upper Plateau Stress (psi) | Distal Portion Plateau Force (lbs) | Filamentary Diameter (in) | Cross-Sectional Area (in$^2$) | Ultimate Tensile Strength (psi) | Break Force (lbs) |
| 0.0082 | $5.28 \times 10^{-5}$ | 85,000 | 4.5 | 0.0045 | $1.59 \times 10^{-5}$ | 340,000 | 5.4 |

For the above-described embodiment, the support coil column strength was found to be sufficient to resist skewing when compressed by the tensile force applied by the core-wire.

EXAMPLE 3

A snare device similar to that of Example 2, but larger in diameter, was constructed. The core-wire of the snare device was made of NITINOL™ nickel-titanium alloy, with the proximal portion of the core-wire having a uniform filamentary cross-sectional diameter of 0.0148 in and with the distal portion of the core-wire having a uniform filamentary cross-sectional diameter of 0.0098 in. Consequently, the filamentary cross-sectional area of the distal portion of the core-wire was $7.54 \times 10^{-5}$ in$^2$. The upper plateau stress for the distal portion of the core-wire was 77,700 psi. As a result, the plateau force for the distal portion of the core-wire was 5.9 lbs.

The support of the subject snare device was in the form of a coil made of a stainless steel wire of round cross-section having an ultimate tensile strength of 344,000 psi. The support had a uniform overall outer diameter of 0.0263 in and a uniform overall inner diameter of 0.0163 in. Consequently, the filamentary cross-sectional diameter of the support was 0.0050 in, and the filamentary cross-sectional area of the support was $1.96 \times 10^{-5}$ in'. As noted above, the ultimate tensile strength of the support was 344,000 psi. As a result, the break force for the support was 6.8 lbs, which is greater than the plateau force of 5.9 lbs. Table 3 below summarizes some of the above-noted values.

TABLE 3

| | Core-wire | | | | Support | | |
|---|---|---|---|---|---|---|---|
| Distal Portion Diameter (in) | Distal Portion Cross-Sectional Area (in$^2$) | Distal Portion Upper Plateau Stress (psi) | Distal Portion Plateau Force (lbs) | Filamentary Diameter (in) | Cross-Sectional Area (in$^2$) | Ultimate Tensile Strength (psi) | Break Force (lbs) |
| 0.0098 | 7.54 × 10$^{-5}$ | 77,700 | 5.9 | 0.0050 | 1.96 × 10$^{-5}$ | 344,000 | 6.8 |

For the above-described embodiment, the support coil column strength was found to be sufficient to resist skewing when compressed by the tensile force applied by the core-wire.

COMPARATIVE EXAMPLE A

A snare device similar to that of Example 2, but whose core-wire has a distal portion of larger diameter, was constructed. The core-wire of the snare device was made of NITINOL™ nickel-titanium alloy, with the proximal portion of the core-wire having a uniform filamentary cross-sectional diameter of 0.0121 in and with the distal portion of the core-wire having a uniform filamentary cross-sectional diameter of 0.0090 in. Consequently, the filamentary cross-sectional area of the distal portion of the core-wire was 6.36×10$^{-5}$ in'. The upper plateau stress for the distal portion of the core-wire was 85,000 psi. As a result, the plateau force for the distal portion of the core-wire was 5.4 lbs.

The support of the subject snare device was in the form of a coil made of a stainless steel wire of round cross-section having an ultimate tensile strength of 340,000 psi. The support had a uniform overall outer diameter of 0.0226 in and a uniform overall inner diameter of 0.0136 in. Consequently, the filamentary cross-sectional diameter of the support was 0.0045 in, and the filamentary cross-sectional area of the support was 1.59×10$^{-5}$ in'. As noted above, the ultimate tensile strength of the support was 340,000 psi. As a result, the break force for the support was 5.4 lbs, which is equal to the plateau force of 5.4 lbs. Table 4 below summarizes some of the above-noted values.

TABLE 4

| | Core-wire | | | | Support | | |
|---|---|---|---|---|---|---|---|
| Distal Portion Diameter (in) | Distal Portion Cross-Sectional Area (in$^2$) | Distal Portion Upper Plateau Stress (psi) | Distal Portion Plateau Force (lbs) | Filamentary Diameter (in) | Cross-Sectional Area (in$^2$) | Ultimate Tensile Strength (psi) | Break Force (lbs) |
| 0.0090 | 6.36 × 10$^{-5}$ | 85,000 | 5.4 | 0.0045 | 1.59 × 10$^{-5}$ | 340,000 | 5.4 |

Figure 20:
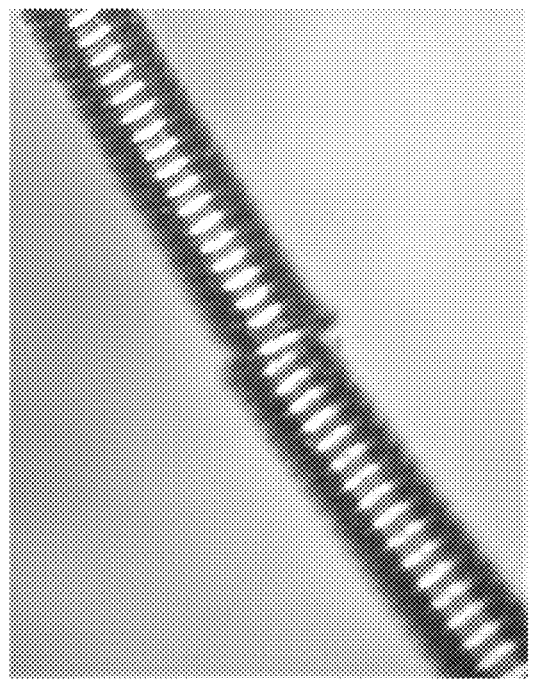
FIG. 20 is a photo showing a portion of the skewed support of the snare device of Comparative Example A.

For the above-described device, after many actuations, the device eventually skewed. FIG. 20 is a photo showing the skewed support of this device.

The embodiments of the present invention described above are intended to be merely exemplary and those skilled in the art shall be able to make numerous variations and modifications to it without departing from the spirit of the present invention. For example, features from one or more of the embodiments described above may be combined in various permutations. All such variations and modifications are intended to be within the scope of the present invention as defined in the appended claims.

What is claimed is:

1. An instrument comprising:
(a) a longitudinally extending support defining an axis, the support having an uncompressed state of comparatively greater length and a compressed state of comparatively lesser length, the support comprising a flexible distal section, the flexible distal section comprising a coiled filament of round cross-sectional shape and defining a first path relative to the axis when in the compressed state, the flexible distal section having a tensile strength, a filamentary cross-sectional area, and a break load, wherein the break load of the flexible distal section is equal to the tensile strength of the flexible distal section multiplied by the filamentary cross-sectional area of the flexible distal section;

(b) a core-wire extending along the axis and anchored to the flexible distal section of the support, the core-wire having a relaxed state of comparatively lesser length and a tensioned state of comparatively greater length, the core-wire comprising a proximal portion and a distal portion, the distal portion of the core-wire defining a second path relative to the axis when in the relaxed state, wherein the second path differs from the first path and includes a looped shape, wherein the distal portion of the core-wire has a filamentary diameter and a filamentary cross-sectional area, wherein the distal portion of the core-wire also has an upper plateau stress in response to a tensile force applied thereto, wherein a plateau force of the distal portion of the core-wire is equal to the upper plateau stress multiplied by the filamentary cross-sectional area of the distal portion of the core-wire, wherein the distal portion of the core-wire has a length, and wherein the filamentary diameter of the distal portion of the core-wire is substantially uniform over the length of the distal portion of the core-wire in the relaxed state; and (c) an actuator secured to a proximal end of the core-wire and to a proximal end of the support to selectively apply both a tensile force to the core-wire and a compressive force to the support, the tensile force causing the core-wire to transition from its relaxed state to its tensioned state, the compressive force causing the support to transition from its uncompressed state to its compressed state;

(d) wherein the break load of the flexible distal section of the support is greater than the plateau force of the distal portion of the core-wire.

2. The instrument as claimed in claim 1 wherein the support terminates distally at a distal end, wherein the core-wire terminates distally at a distal end, and wherein the distal end of the core-wire is anchored to the distal end of the support.

3. The instrument as claimed in claim 1 wherein the support terminates distally at a distal end, wherein the core-wire terminates distally at a distal end, and wherein the distal end of the core-wire is anchored to the support at a distance proximal to the distal end of the support.

4. The instrument as claimed in claim 1 wherein the looped shape is generally circular.

5. The instrument as claimed in claim 1 wherein the looped shape comprises a conical helix.

6. The instrument as claimed in claim 1 wherein the looped shape comprises a cylindrical helix.

7. The instrument as claimed in claim 1 wherein the looped shape comprises a proximal cylindrical helix and a distal conical helix.

8. The instrument as claimed in claim 1 wherein the proximal portion of the core-wire has a first strain in response to a tensile force, wherein the distal portion of the core-wire has a second strain in response to the tensile force, and wherein the first strain is less than the second strain.

9. The instrument as claimed in claim 8 wherein the core-wire comprises a superelastic material, wherein the first strain is in an initial elastic region, and wherein the second strain is in a superelastic region.

10. The instrument as claimed in claim 9 wherein the core-wire is a one-piece structure comprising a nickel-titanium alloy, with the proximal portion of the core-wire having a filamentary diameter of comparative greater dimension and with the distal portion of the core-wire having a filamentary diameter of comparatively lesser dimension.

11. The instrument as claimed in claim 1 wherein at least a portion of the core-wire is coated with a lubricious coating.

12. The instrument as claimed in claim 1 wherein the first path is a straight line.

13. The instrument as claimed in claim 1 wherein the support further comprises a proximal portion, the proximal portion of the support and the distal portion of the support forming a one-piece structure.

14. The instrument as claimed in claim 13 wherein the support further comprises a sleeve, the sleeve being disposed around at least one of the proximal portion of the support and the distal portion of the support.

15. The instrument as claimed in claim 1 wherein the actuator comprises a handle and a slide, the slide being slidably mounted on the handle to be selectively moved proximally and distally, the proximal end of the core-wire being coupled to the handle, the proximal end of the support being coupled to the slide.

16. The instrument as claimed in claim 1 wherein the actuator further comprises an anchor, the proximal end of the core-wire being secured to the anchor, the anchor being rotatably mounted on the handle, whereby tension applied to the core-wire is adjusted by rotating the anchor.

17. The instrument as claimed in claim 1 further comprising a spacer coil mounted around the distal portion of the core-wire and interior relative to the support.

* * * * *